(12) United States Patent
Feller et al.

(10) Patent No.: US 6,596,734 B1
(45) Date of Patent: Jul. 22, 2003

(54) TETRAHYDROISOQUINOLINE COMPOUNDS FOR USE AS β₃-ADRENORECEPTOR AGONISTS

(75) Inventors: Dennis R. Feller, Oxford, MS (US); Duane D. Miller, Germantown, TN (US)

(73) Assignee: Molecular Design International, Inc., Memphis, TN (US)

( * ) Notice: Subject to any disclaimer, the term of this patent is extended or adjusted under 35 U.S.C. 154(b) by 0 days.

(21) Appl. No.: 10/269,438

(22) Filed: Oct. 11, 2002

Related U.S. Application Data

(63) Continuation-in-part of application No. 10/149,953, filed as application No. PCT/US01/10376 on Mar. 29, 2001.

(51) Int. Cl.⁷ .................. C07D 221/02; A61K 31/47
(52) U.S. Cl. ........................ 514/310; 546/143
(58) Field of Search .................. 546/143; 514/310

(56) References Cited

U.S. PATENT DOCUMENTS

| | | | |
|---|---|---|---|
| 3,337,539 | A | 8/1967 | Mészáros et al. |
| 3,438,989 | A | 4/1969 | Shavel, Jr. et al. |
| 3,497,516 | A | 2/1970 | Mashimo et al. |
| 3,647,799 | A | 3/1972 | Watanabe et al. |
| 3,818,015 | A | 6/1974 | Yamato et al. |
| 3,872,130 | A | 3/1975 | Kreighbaum et al. |
| 3,873,704 | A | 3/1975 | Yamato et al. |
| 3,910,915 | A | 10/1975 | Yonan |
| 3,910,927 | A | 10/1975 | Kreighbaum et al. |
| 3,988,339 | A | 10/1976 | Kaiser et al. |
| 4,054,659 | A | 10/1977 | Ikezaki et al. |
| 4,321,254 | A | 3/1982 | Ali |
| 4,442,108 | A | 4/1984 | Le Polles et al. |
| 4,525,589 | A | 6/1985 | Hidaka et al. |
| 4,536,510 | A | 8/1985 | Wasserman et al. |
| 4,666,918 | A | 5/1987 | Ivanova et al. |
| 4,707,485 | A | 11/1987 | Kaiser et al. |
| 4,737,504 | A | 4/1988 | Miller et al. |
| 4,798,897 | A | 1/1989 | Hidaka et al. |
| 4,812,573 | A | 3/1989 | Durant et al. |
| 4,857,301 | A | 8/1989 | Czarniecki et al. |
| 5,059,608 | A | 10/1991 | Takasugi et al. |
| 5,177,085 | A | 1/1993 | Naef |
| 5,210,088 | A | 5/1993 | Minchin et al. |
| 5,238,935 | A | 8/1993 | Dugar et al. |
| 5,246,943 | A | 9/1993 | Blankley et al. |
| 5,272,270 | A | 12/1993 | Hirsenkorn et al. |
| 5,340,811 | A | 8/1994 | Kajihara et al. |
| 5,350,757 | A | 9/1994 | Blankley et al. |
| 5,362,736 | A | 11/1994 | Ishikawa et al. |
| 5,446,164 | A | 8/1995 | Ishikawa et al. |
| 5,498,717 | A | 3/1996 | Ishikawa et al. |
| 5,519,034 | A | 5/1996 | Kozlik et al. |
| 5,525,614 | A | 6/1996 | Blankley et al. |
| 5,707,985 | A | 1/1998 | McKenzie et al. |
| 5,750,520 | A | 5/1998 | Danilewicz et al. |
| 5,756,516 | A | 5/1998 | Liu et al. |
| 5,798,352 | A | 8/1998 | Danilewicz |
| 5,804,586 | A | 9/1998 | Sargent et al. |
| 5,807,868 | A | 9/1998 | Sargent et al. |
| 5,880,285 | A | 3/1999 | Broger et al. |
| 5,929,085 | A | 7/1999 | MacDonald et al. |
| 6,043,253 | A | 3/2000 | Brockunier et al. |
| 6,063,925 | A | 5/2000 | Demian et al. |
| 6,127,381 | A | 10/2000 | Basu et al. |
| 6,153,608 | A | 11/2000 | Hidaka et al. |
| 6,248,754 | B1 | 6/2001 | Coulton et al. |
| 6,274,594 | B1 | 8/2001 | Coulton et al. |
| 6,277,861 | B1 | 8/2001 | Harling et al. |
| 2001/0039285 | A1 | 11/2001 | Cameron et al. |
| 2001/0039289 | A1 | 11/2001 | Blok et al. |

FOREIGN PATENT DOCUMENTS

| | | |
|---|---|---|
| EP | 0 210 827 A2 | 2/1987 |
| JP | 47018898 | 9/1972 |
| JP | 52095676 | 8/1977 |
| WO | WO 99/16752 | 4/1999 |
| WO | WO 99/44609 A1 | 9/1999 |

OTHER PUBLICATIONS

Adejare, et al., "Syntheses and β–Adrenergic Agonist and Antiaggregatory Properties of N–Substituted Trimetoquinol Analogues[1]", *J. Med. Chem.*, 1986, pp. 1603–1609, vol. 29.

Ahn, et al., "Characterization of the Inhibition of U46619–Mediated Human Platelet Activation by the Trimetoquinol Isomers", *Biochemical Pharmacology*, 1988, pp. 3023–3033, vol. 37, No. 15.

(List continued on next page.)

*Primary Examiner*—Zinna Northington Davis
(74) *Attorney, Agent, or Firm*—Alston & Bird LLP

(57) ABSTRACT

The invention provides compounds of formula:

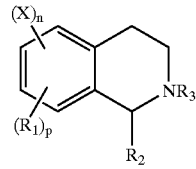

wherein $R_1$ is —NHS(O)$_m$R, wherein R is alkyl, substituted alkyl, alkoxy, substituted alkoxy, cycloalkyl, substituted cycloalkyl, aryl, substituted aryl, heteroaryl, substituted heteroaryl, heterocycle, or substituted heterocycle; X is independently selected from the group consisting of halo, alkyl, substituted alkyl, alkoxy, substituted alkoxy, hydroxy, nitro, amino, and substituted amino; $R_2$ is benzyl or benzyl substituted with one or more substituents selected from the group consisting of halo, $CF_3$, hydroxy, nitro, alkoxy, substituted alkoxy, alkyl, substituted alkyl, cycloalkyl, substituted cycloalkyl, aryl, substituted aryl, heteroaryl, substituted heteroaryl, heterocycle, substituted heterocycle, amino, and substituted amino of formula —NHR' or —NR'R', wherein each R' is alkyl, substituted alkyl, —C(O)Y, —C(O)NHY, or —C(O)SY, wherein Y is alkyl or substituted alkyl; $R_3$ is H or alkyl; n is 0–3; m is 1–2; p is 1–4; the sum of n and p is 1–4; and pharmaceutically acceptable salts thereof.

66 Claims, No Drawings

OTHER PUBLICATIONS

Christoff, et al., "Synthesis and Evaluation of Trimetoquinol Derivatives: Novel Thromboxane $A_2$/Prostaglandin $H_2$ Antagonists with Diminished β–Adrenergic Agonist Activity", *J. Med. Chem.*, 1997, vol. 40, pp. 85–91.

Clark, et al., "5–Fluoro– and 8–Fluorotrimetoquinol: Selective $β_2$–Adrenoceptor Agonists", *J. Med. Chem.*, 1987, pp. 86–90, vol. 30.

De Los Angeles, et al., "Iodinated Analogs of Trimetoquinol as Highly Potent and Selective $β_2$–Adrenoceptor Ligands", *J. Med. Chem.*, 1996, vol. 39, pp. 3701–3711.

Fraundorfer, et al., "Biochemical and Pharacololgical Characterization of High–Affinity Trimetoquinol Analogs on Guinea Pig and Human Beta Adrenergic Receptor Subtypes: Evidence for Partial Agonism[1] ", *J. Pharmacology and Experimental Therapeutics*, 1994, pp. 665–674, vol. 270, No. 2.

Fraundorfer, Paul F., "Functional and Biochemical Characterization of Trimetoquinol (TMQ) Analog Interactions with β–Adrenergic Receptor Subtypes", A Dissertation, The Ohio State University, 1993.

Gavai, et al. "BMS–196085: A Potent and Selective Full Agonist of the Human $β_3$ Adrenergic Receptor", *"Bioorg. Med. Chem. Lett."*, 2001, pp. 3041–3044, vol. 11.

Harrold, et al., "Synthesis and Platelet Antiaggregatory Activity of Trimetoquinol Analogs as Endoperoxide/Thromboxane $A_2$ Antagonists", *Drug Design and Delivery*, 1987, pp. 193–207, vol. 1.

He, et al., "Synthesis and Human β–Adrenoceptor Activity of 1–(3,5–Diiodo–4–methoxybenzyl)–1,2,3,4–tetrahydroisoquiniolin–6–ol Derivatives In Vitro", *J. Med. Chem.,*, 2000, pp. 591–598, vol. 43, No. 4.

He, et al., "Synthesis and Human β–Adrenoceptor Activity of 1,2,3,4–Tetrahydroisoquinoline–6–ol Derivatives, In Vitro", *Am. Chem. Soc.*, 218th ACS National Meeting, Aug. 22–26, 1999, Abstract.

Howe, Ralph, "$β_3$–Adrenergic agonists", *Drugs of the Future*, 1993, pp. 529–549, vol. 18, No. 6.

Hu, et al., "(4–Piperidin–1–yl)phenyl Amides: Potent and Selective Human $β_3$ Agonists", *J. Med. Chem.*, 2001, pp. 1456–1466, vol. 44, No. 9.

Ishiwata, et al., "Synthesis of Aminoisoquinolines and Related Compounds. IX. Synthesis of (+–)–0–methylcaseadine", *Chem. Pharm. Bull.*, 1970, vol. 18(9), Abstract.

Ishiwata, et al., "Syntheses of Aminoisoquinolines and Related Compounds. VI. A Modified Synthesis of dl–pronuciferine", *Chem. Pharm. Bull.*, 1970, vol. 18(6), Abstract.

Ishiwata, et al., "Syntheses of Aminoisoquinolines and Related Compounds. II. Syntheses of 6–amino–1–benzylisoquinolines by the Bischler–Napieralski reaction", *Chem. Pharm. Bull.*, 1969, vol. 17(11), Abstract.

Iwasawa, et al., Studies on Tetrahydroisoquinolines (THI) (I) Bronchodilator Activity and Structure–Activity Relationship, *Jap. J. Pharmacol.*, 1967, pp. 143–152, vol. 17.

Kajigaeshi, et al., Halogenation Using Quaternary Ammonium Polyhalides. VII. [1)]Iodination of Aromatic Amines by Use of Benzyltrimethylammonaium Dichloroiodate(1–), *Bull. Chem. Soc. Jpn.*, 1988, pp. 600–602, vol. 61, No. 2.

Konkar, et al., "β–Adrenoceptor Subtype Activities of Trimetoquinol Derivatives: Biochemical Studies on Human β–Adrenoceptors Expressed in Chinese Hamster Ovary Cells", *J. Pharamacology and Experimental Therapeutics*, 1999, pp. 875–883, vol. 291, No. 2.

Mayo, et al., "Stereo–Dependent Inhibition of Human Platelet Function by the Optical Isomers of Trimetoquinol", *Biochemical Pharamacolgoy*, 1981, pp. 2237–2241, vol. 30, No. 16.

Memetzidis, et al., "Synthesis of Aromatic Chloroberbines", *Heterocycles*, 1990, vol. 31(2), Abstract.

Mehta, et al., "Biochemical and Functional Characterization of 1–Benzyl Substituted Trimetoquinol Affinity Analogs of Rat and Human β–Adrenoceptors, " *Biochemical Pharamcology*, 2000, pp. 517–529, vol. 59.

Nikulin et al., "A Shortened Approach to Parallel Synthesis of Tetrahydroisoquinolines (THI) Via Bishler–Napieralski Cyclization", *Am. Chem. Soc.*, 215th ACS National Meeting, Mar. 29–Apr. 2, 1998.

Nikulin, et al., "7–Substituted 1–Aryl–1,2,3,4–tetrahydroisoquinolin–6–ols as Selective Agonists for Human $β_3$–Adrenoceptor", *Am. Chem. Soc.*, 219th ACS National Meeting, Mar. 26–30, 2000.

Shin, et al., "Interactions of Nonprostanoid Trimetoquinol Analogs with Thromboxane $A_2$/Prostaglandin $H_2$ Receptors in Human Platelets, Rat Vascular Endothelial Cells and Rat Vascular Smooth Muscle Cells[1]", *J. Pharmacology and Experimental Therapeutics*, 1993, pp. 1017–1023, vol. 267, No. 3.

Shin, et al., "Stereospecific Interactions of Nonprostanoid Trimetoquinol Analogs With Thromboxane $A_2$/Prostaglandin $H_2$ Receptor Sites in Human and Rat Platelets, and Rat Vascular Endotheial and Smooth Muscle Cells", *Pharmacology Communications*, 1992, pp. 303–312, vol. 1, No. 4.

Shin, et al., "Pharmacologic Antagonism of Thromboxane $A_2$ Receptors by Trimetoquinol Analogs In Vitro and In Vivo", *Chirality*, 1991, pp. 112–117, vol. 3.

Van Baak, et al., "Acute effect of L–796568, a novel $β_3$–adrenergic receptor agonist, on engergy expenditure in obese men", *Clinical Pharmacology & Therapeutics*, 2002, pp. 272–279, vol. 71, No. 4.

Washburn, et al., "Beta 3 Agonists. Part 1: Evolution from Inception to BMS–19449", *"Bioorg. Med. Chem. Lett."*, 2001, pp. 3035–3039, vol. 11.

Yamato, et al., "Synthesis of 6,7–Dihydroxy–1,2,3,4–Tetrahydroisoquinoline Derivatives", *Tetrahedron*, 1966, pp. 129–134, Suppl. 8, Part 1.

Zheng, et al. "2–Amino–4–benzyl–4,5,6,7–tetrahydrothiazolo[5,4–c]pyridines: Novel Selective $β_3$–Adrenoceptor Agonists", *J. Med. Chem.*, 1999, pp. 2287–2294, vol. 42, No. 12.

Zheng, et al., "2–Amino–4–Aryl–4,5,6,7–Tetrahydrothiazolo[5,4–c]Pyridines: Proposed Novel Catechol Bioisosteric Analogs of Trimetoquinol (TMQ)—A Potent β–Adrenoceptor Agonist and TP Receptor Antagonist", *Am. Chem. Soc.*, 1995 Joint Southeast–Southwest Regional Meeting, Nov. 29–Dec. 1, 1995, Abstract.

TETRAHYDROISOQUINOLINE COMPOUNDS FOR USE AS β₃-ADRENORECEPTOR AGONISTS

CROSS-REFERENCE TO RELATED APPLICATIONS

This Application is a continuation-in-part of U.S. application Ser. No. 10/149,953, filed on Jun. 17, 2002, which is a national phase application of International Application No. PCT/US01/10376, filed Mar. 29, 2001, both of which are incorporated by reference herein in their entirety.

FIELD OF THE INVENTION

The invention relates to compounds useful as β₃-adrenoreceptor agonists.

BACKGROUND OF THE INVENTION

For many individuals, a tendency to experience weight problems and even obesity is often symptomatic of disease or disorders of the metabolism associated with serious and even life-threatening conditions. The decade of the 1990's witnessed dramatic increases in diabetes and obesity in the United States, and at the same time, Americans showed little improvement in eating habits or increasing their physical activity. In a study published in the Journal of the American Medical Association, the Center for Disease Control and Prevention (CDC) found a 61 percent increase in the percentage of Americans who are obese from 1991 to 2000 (12.0 percent to 19.8 percent), and a 49 percent increase in the percentage of Americans who have diabetes from 1990 to 2000 (4.9 percent to 7.3 percent). About nine percent of the national health care expenditures in the United States are directly related to obesity and physical inactivity. In 1997, the health care costs associated with diabetes were $98 billion.

A wide variety of approaches to the alleviation of obesity have ebbed and flowed though modem culture, ranging from a diverse collection of dietary strategies, to drugs, to surgical interventions, to hypnosis. All have met with indifferent success at best. A great deal of the difficulty in the art and practice of obesity and weight management has been a consequence of attention focused on the control of appetite, and reducing the amount of food intake. It has long been the belief of many that only by the control of caloric intake is it possible to regulate body weight and fat deposition and utilization. Since appetite is controlled and regulated in the brain, brain pharmacology and the alteration of brain chemistry has been a primary focus of weight regulation and control efforts. Only in very recent times has obesity been addressed in relation to the metabolic pathways of the body and their role and import in fat storage and usage in the body.

Recent research has elucidated some of the mechanisms of obesity and weight gain, and has revealed that much of the limitation of prior and current weight-loss techniques stems from the fact that they are biochemically, and particularly metabolically, unsound and incapable of stimulating, regulating and modulating metabolism of fats in adipose tissues. Increasing efforts have been directed to biochemical research into the mechanisms of fat deposition and metabolism.

Among the biochemical work of note has been the recent recognition of a role of β-adrenoreceptor activity in the metabolism of fats. It has been recognized that agonists for β-adrenoreceptors have, in some cases, produced marked weight loss in animals, particularly humans and other mammals. More recently, the loss of weight has been identified with the β-adrenoreceptor sub-type, β₃-adrenoreceptor. It has been demonstrated that compounds that are significant β₃-adrenoreceptor agonists produce marked weight loss in animals, particularly humans and other mammals, and that the loss is sustained with continuation of the administration of such compounds. These compounds provide potent regulation of fat metabolism. The compounds employed to date are also agonists for the β₁-adrenoreceptor and the β₂-adrenoreceptor sites. The lack of selectivity represents unwanted side effects of such compounds, and the compounds known as β₃-adrenoreceptor agonists to-date are not suitable candidates for therapeutic usage because of undesirable side effects.

There is a need in the art for therapeutic agents that are highly potent and highly selective β₃-adrenoreceptor agonists for effective stimulation, regulation and modulation of metabolism of fats in adipose tissues.

SUMMARY OF THE INVENTION

The present invention provides tetraisoquinoline compounds useful as β₃-adrenoreceptor agonists. In a preferred embodiment, the compounds of the invention are highly specific β₃-adrenoreceptor agonists that exhibit little or no affinity for the other β-adrenoreceptors.

In one aspect, the present invention provides compounds of the formula:

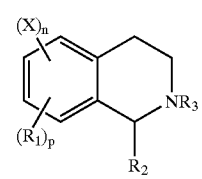

Formula I wherein:
each $R_1$ is —NHS(O)$_m$R, wherein R is alkyl, substituted alkyl, alkoxy, substituted alkoxy, cycloalkyl, substituted cycloalkyl, aryl, substituted aryl, heteroaryl, substituted heteroaryl, heterocycle, or substituted heterocycle;

each X is independently selected from the group consisting of halo, alkyl, substituted alkyl, alkoxy, substituted alkoxy, hydroxy, nitro, amino, and substituted amino;

$R_2$ is benzyl or benzyl substituted with one or more substituents selected from the group consisting of halo, $CF_3$, hydroxy, nitro, alkoxy, substituted alkoxy, alkyl, substituted alkyl, cycloalkyl, substituted cycloalkyl, aryl, substituted aryl, heteroaryl, substituted heteroaryl, heterocycle, substituted heterocycle, amino, and substituted amino of formula —NHR' or —R'R', wherein each R' is alkyl, substituted alkyl, —C(O)Y, —C(O)NHY, or —C(O)SY, wherein Y is alkyl or substituted alkyl;

$R_3$ is H or alkyl;

n is 0–3;

m is 1–2;

p is 1–4;

the sum of n and p is 1–4;

and pharmaceutically acceptable salts thereof.

In another aspect, the invention provides pharmaceutical compositions comprising at least one compound of Formula I and at least one pharmaceutically acceptable carrier. In a further aspect, the invention provides a method of treating obesity and related conditions that would benefit from stimulating, regulating and modulating metabolism of fats in adipose tissues, specifically by interaction with the $\beta_3$-adrenoreceptor. The method involves administering a compound of Formula I, optionally with one or more pharmaceutically acceptable carriers, to an animal, preferably a human or other mammal.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. Definitions

The following terms as used herein have the meanings indicated.

As used in the specification, and in the appended claims, the singular forms "a", "an", "the", include plural referents unless the context clearly dictates otherwise.

The term "alkyl" refers to hydrocarbon chains typically ranging from about 1 to about 12 carbon atoms in length, preferably 1 to about 6 atoms, and includes straight and branched chains. The hydrocarbon chains may be saturated or unsaturated.

"Cycloalkyl" refers to a saturated or unsaturated cyclic hydrocarbon chain, including bridged, fused, or spiro cyclic compounds, preferably comprising 3 to about 12 carbon atoms, more preferably 3 to about 8.

The term "substituted alkyl" or "substituted cycloalkyl" refers to an alkyl or cycloalkyl group substituted with one or more non-interfering substituents, such as, but not limited to, C3–C8 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like.

"Alkoxy" refers to an —O—R group, wherein R is alkyl or substituted alkyl, preferably C1–C6 alkyl (e.g., methoxy or ethoxy).

"Aryl" means one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents. For substitutions on a phenyl ring, the substituents may be in any orientation (i.e., ortho, meta or para).

"Heteroaryl" is an aryl group containing from one to four heteroatoms, preferably N, O, or S, or a combination thereof, which heteroaryl group is optionally substituted at carbon or nitrogen atom(s) with C1–6 alkyl, —CF$_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3, 5-triazine); and 6-membered heteroaryls with four heteroatoms.

"Substituted heteroaryl" is heteroaryl having one or more non-interfering groups as substituents.

"Heterocycle" or "heterocyclic" means one or more rings of 5–12 atoms, preferably 5–7 atoms, with or without unsaturation or aromatic character and at least one ring atom which is not carbon. Preferred heteroatoms include sulfur, oxygen, and nitrogen. Multiple rings may be fused, as in quinoline or benzofuran.

"Substituted heterocycle" is heterocycle having one or more side chains formed from non-interfering substituents.

"Non-interfering substituents are those groups that, when present in a molecule, are typically non-reactive with other functional groups contained within the molecule.

Suitable non-interfering substituents or radicals include, but are not limited to, halo, C1–C10 alkyl, C2–C10 alkenyl, C2–C10 alkenyl, C1–C10 alkoxy, C7–C12 aralkyl, C7–C12 alkaryl, C3–C10 cycloalkyl, C3–C10 cycloalkenyl, phenyl, substituted phenyl, toluoyl, xylenyl, biphenyl, C2–C12 alkoxyalkyl, C7–C12 alkoxyaryl, C7–C12 aryloxyalkyl, C6–C12 oxyaryl, C1–C6 alkylsulfonyl, C1–C10 alkylsulfonyl, —(CH$_2$)$_m$—O—(C1–C10 alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C1–C10 alkyl), —C(O)—(C1–C10 alkyl), C2–C10 thioalkyl, —C(O)O—(C1–C10 alkyl), —OH, —SO$_2$, =S, —COOH, —NR, carbonyl, —C(O)—(C1–C10 alkyl)—CF$_3$, —C(O)—CF$_3$, —C(O)NR$_2$, —(C1–C10 alkyl)—S—(C6–C12 aryl), —C(O)—(C6–C12 aryl), —(CH$_2$)$_m$—O—(CH$_2$)$_m$—O—(C1–C10 alkyl) wherein each m is from 1 to 8, —C(O)NR, —C(S)NR, —SO2NR, —NRC(O)NR, —NRC(S)NR, salts thereof, and the like. Each R as used herein is H, alkyl or substituted alkyl, aryl or substituted aryl, aralkyl, or alkaryl.

"Heteroatom" means any non-carbon atom in a hydrocarbon analog compound. Examples include oxygen, sulfur, nitrogen, phosphorus, arsenic, silicon, selenium, tellurium, tin, and boron.

II. Tetrohydroisoquinoline Compounds of the Invention

The present invention provides tetraisoquinoline compounds useful as $\beta_3$-adrenoreceptor agonists, preferably highly selective $\beta_3$-adrenoreceptor agonists, having the formula:

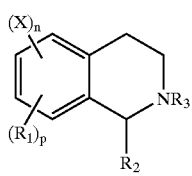

Formula I wherein:
- each $R_1$ is —NHS(O)$_m$R, wherein R is alkyl, substituted alkyl, alkoxy, substituted alkoxy, cycloalkyl, substituted cycloalkyl, aryl, substituted aryl, heteroaryl, substituted heteroaryl, heterocycle, or substituted heterocycle;
- each X is independently selected from the group consisting of halo, alkyl, substituted alkyl, alkoxy, substituted alkoxy, hydroxy, nitro, amino, and substituted amino;
- $R_2$ is benzyl or benzyl substituted with one or more substituents selected from the group consisting of halo, CF$_3$, hydroxy, nitro, alkoxy, substituted alkoxy, alkyl, substituted alkyl, cycloalkyl, substituted cycloalkyl, aryl, substituted aryl, heteroaryl, substituted heteroaryl, heterocycle, substituted heterocycle, amino, and substituted amino of formula —NHR' or —NR'R', wherein each R' is alkyl, substituted alkyl, —C(O)Y, —C(O)NHY, or —C(O)SY, wherein Y is alkyl or substituted alkyl;
- $R_3$ is H or alkyl (e.g., C1–C6 alkyl such as methyl, ethyl and the like);
- n is 0–3, preferably 1;
- m is 1–2, preferably 2;
- p is 1–4, preferably 1;
- the sum of n and p is 1–4, preferably 2;

and pharmaceutically acceptable salts thereof.

As used herein, "substituted amino" encompasses mono- and disubstituted amino groups. Preferred substituents of the "substituted" groups referred to above include, but are not limited to, C1–C6alkyl, C1–C6 alkoxy, hydroxy, halo, nitro, amino, amino substituted with one or two C1–C6alkyl, CF$_3$, —O—CF$_3$, phenyl (optionally substituted with one or more C1–C6alkyl, C1–C6 alkoxy, hydroxy, halo, nitro, CF$_3$, —O—CF3, amino, or amino substituted with one or two C1–C6alkyl), and benzyl (optionally substituted with one or more C1–C6alkyl, C1–C6 alkoxy, hydroxy, halo, nitro, CF$_3$, —O—CF$_3$, amino, or amino substituted with one or two C1–C6alkyl).

Preferred embodiments of the compounds of the invention include a single $R_1$ sulfonamide moiety at the 7-position. The R group of the sulfonamide moiety is preferably C1–C6alkyl, substituted C1–C6alkyl, phenyl, substituted phenyl, benzyl, or substituted benzyl. Particularly preferred R groups include methyl, ethyl, propyl, butyl, phenyl, and benzyl, wherein the phenyl or benzyl group can be substituted with one or more C1–C6alkyl, C1–C6 alkoxy, hydroxy, halo, nitro, CF$_3$, —O—CF$_3$, amino, or amino substituted with one or two C1–C6alkyl.

Each X is preferably C1–C6alkyl, C1–C6alkoxy, hydroxy or halo. In one embodiment, n is 1 and X is a hydroxy located at the 6-position.

The benzyl group of $R_2$ is preferably substituted with one or more C1–C6alkoxy (e.g., methoxy, ethoxy) or halo groups (e.g., bromo, iodo). In one embodiment, the $R_2$ group has the structure:

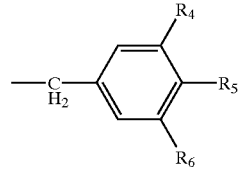

Formula Ia wherein $R_4$, $R_5$, and $R_6$ are independently selected alkoxy or halo. In one preferred embodiment, $R_4$ and $R_6$ are halo, such as bromo, and $R_5$ is C1–C6alkoxy (e.g., methoxy).

As noted above, preferred embodiments include an X group at the 6-position and an $R_1$ group at the 7-position as shown below.

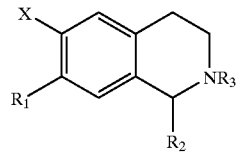

Formula Ib

A particularly preferred embodiment of the invention provides compounds of the structure:

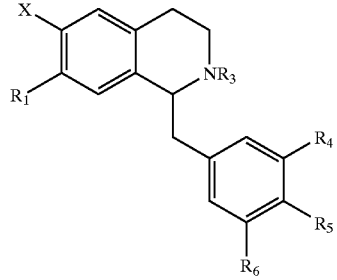

Formula Ic wherein:
- X is hydroxy;
- $R_1$ is —NHS(O)$_2$R, wherein R is selected from the group consisting of C1–C6alkyl, C1–C6alkoxy, phenyl, phenyl substituted with one or more C1–C6alkyl, C1–C6alkoxy, halo, CF$_3$, or —O—CF$_3$, benzyl, and benzyl substituted with one or more C1–C6alkyl, C1–C6alkoxy, halo, CF$_3$, or —O—CF$_3$;
- $R_3$ is H or methyl, preferably H; and
- $R_4$, $R_5$, and $R_6$ are independently selected alkoxy (e.g., methoxy, ethoxy) or halo (e.g., bromo).

While racemic mixtures of compounds of the invention can be active, selective, and bioavailable, isolated isomers are ordinarily of more particular interest. The S(−) isomers are preferred, as they generally provided the highest selectivity and the highest bioavailability. The R(+) isomers are found to be moderately active and retain selectivity, and the R-isomers are in some cases easier to isolate.

The compounds of Formula I may be utilized per se or in the form of a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulphonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group. Salts prepared from maleic acid and hydrochloric acid are particularly preferred.

Exemplary compounds of Formula I above are shown below:

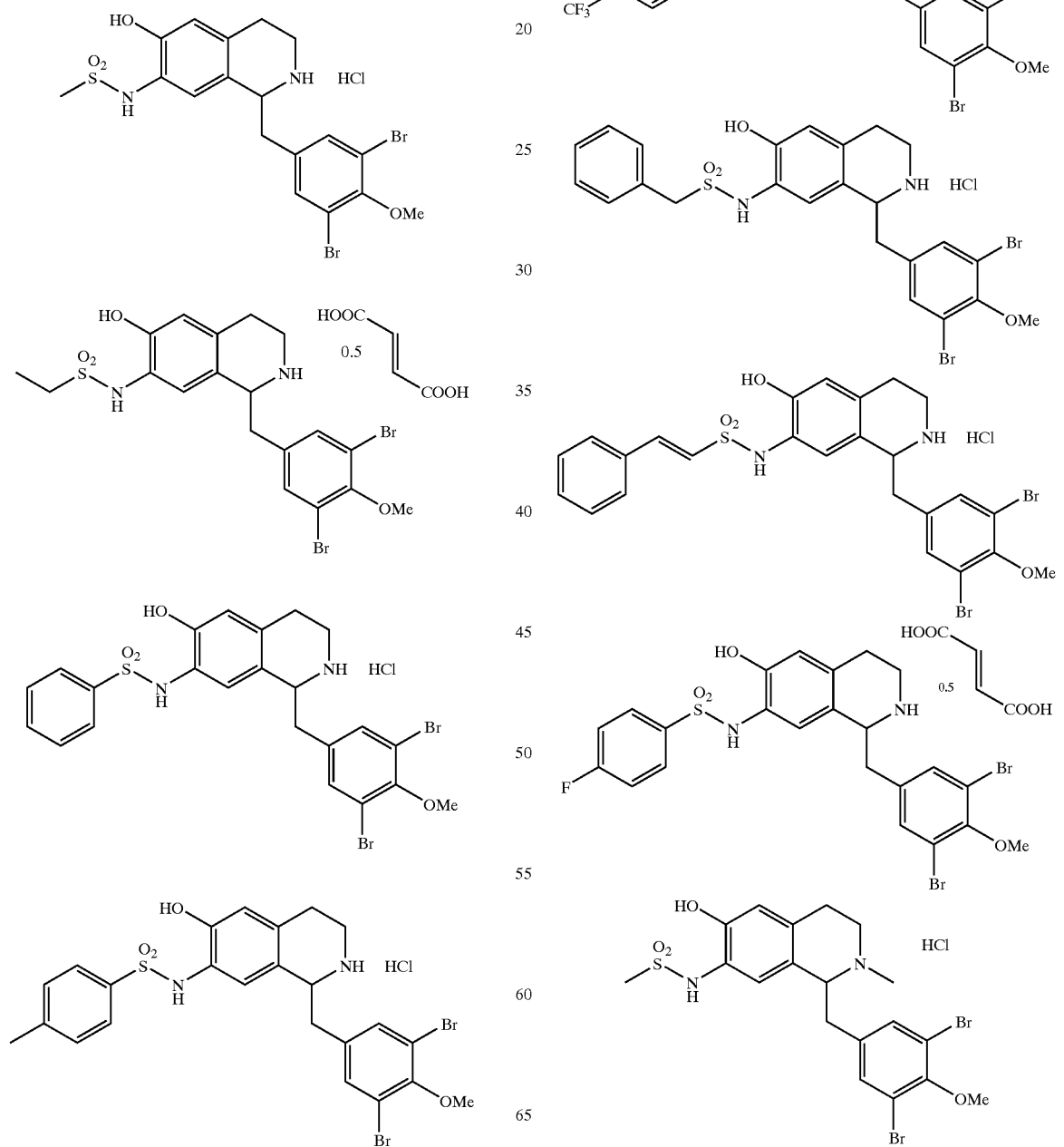

-continued

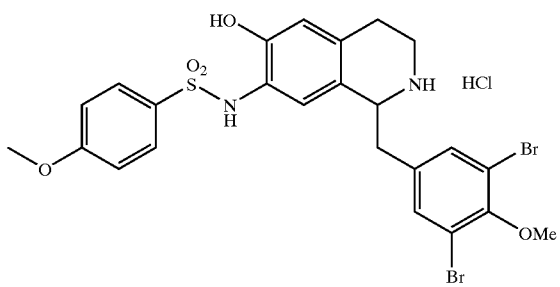

II. Method of Making the Tetrohydroisoquinoline Compounds of the Invention

A convenient protection scheme has been devised for the synthesis of the desired $\beta_3$-adrenoreceptor agonists of the present invention adapted from the procedures disclosed in a previous application assigned to the present assignee and designated U.S. patent application Ser. No. 09/164,047, filed Sep. 30, 1998, which is hereby incorporated by reference herein. As those of ordinary skill in the art of chemical synthesis will understand, the procedures there are adapted to the requirements of the present invention by well-known and readily understood adaptations to accommodate selection and use of differing starting reagents. The synthesis methods are generally adapted from methods disclosed in Clark, M. T.; Adejare, A.; Shams, G.; Feller, D. R.; Miller, D. D. "5-fluoro- and 8fluorotrimetoquinol: selective beta 2-adrenoceptor agonists" J Med Chem 1987, 30, 86–90; Harrold, M. W.; Gerhardt, M. A.; Romstedt, K.; Feller, D. R.; Miller, D. D. "Synthesis and platelet antiaggregatory activity of trimetoquinol analogs as endoperoxide/thromboxane A2 antagonists" Drug Des Deliv 1987,1, 193–207; Adejare,A.; Miller, D. D.; Fedynaj S.;Ahn, C. H.; Feller, D. R. "Syntheses and betaadrenergic agonist and antiaggregatory properties of N-substituted trimetoquinol analogues" J Med Chem 1986,29,1603–9.

As illustrated in the appended examples, compounds of the invention can be formed using N-[2-(4-amino-3-benzyloxy-phenyl)-ethyl]-2-(3,5-dibromo-4-methoxyphenyl)-acetamide as a starting point, which can be synthesized as disclosed in Example 1. Isolation of the stereoisomers is performed by known techniques, including recrystallization using diasteromeric salts, chiral column separation using HPLC, adsorption chromatography, and the like.

IV. Pharmaceutical Compositions

In another aspect, the invention provides pharmaceutical formulations or compositions, both for veterinary and for human medical use, comprising a compound of Formula I as described above and one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), and in "Handbook of Pharmaceutical Excipients", Third Ed., Ed. A. H. Kibbe, Pharmaceutical Press, 2000.

The compounds of Formula I above may be formulated in compositions including those suitable for oral, buccal, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing a compound of Formula I into association with a carrier that constitutes one or more accessory ingredients. In general, the compositions are prepared by bringing a compound of the invention into association with a liquid carrier to form a solution or a suspension, or alternatively, bringing a compound of the invention into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of the compound of Formula I in the formulation will vary depending the specific compound selected, dosage form, target patient population, and other considerations, and will be readily determined by one skilled in the art. The amount of the compound of Formula I in the formulation will be that amount necessary to deliver a therapeutically effective amount of the compound to a patient in need thereof to achieve at least one of the therapeutic effects associated with the compounds of the invention. In practice, this will vary widely depending upon the particular compound, its activity, the severity of the condition to be treated, the patient population, the stability of the formulation, and the like. Compositions will generally contain anywhere from about 1% by weight to about 99% by weight of a compound of the invention, typically from about 5% to about 70% by weight, and more typically from about 10% to about 50% by weight, and will also depend upon the relative amounts of excipients/additives contained in the composition.

V. Method of Using the Tetrohydroisoquinoline Compounds of the Invention

In a further aspect, the present invention relates to the field of treating obesity and overweight conditions in animals, particularly humans and other mammals, and associated effects of conditions associated with obesity and overweight, including Type II diabetes mellitus (non-insulin dependent diabetes), insulin resistance, glucose intolerance, hypothyroidism, morbid obesity, and the like.

The regulatory and modulatory effect of the compounds of the present invention are believed to be dependent on continued administration over time, and the attainment of an equilibrium state which is believed to be dose dependent. In that fashion, the present invention affords the control of body fat in animals, particularly humans and other mammals, over sustained periods, at desirable levels of body fat and/or body mass indices, as defined in the medical literature.

The compounds can be formulated into pharmaceutical compositions to serve as highly selective, effective and safe $\beta_3$-adrenoreceptor agonists to provide long-term weight control. In humans, the compositions can be administered to control body fat levels, and to maintain acceptable body fat levels over time. In domesticated animals, the compositions can be administered to attain desirably low fat content in carcass meats intended for human consumption.

The method of treatment generally includes administering a therapeutically effective amount of a compound of Formula I, optionally in a pharmaceutical composition including one or more pharmaceutically acceptable carriers. The therapeutically effective amount is preferably sufficient to stimulate, regulate and modulate metabolism of fats in adipose tissues. The therapeutically effective dosage amount of any specific formulation will vary somewhat from drug to drug, patient to patient, and will depend upon factors such as the condition of the patient and the route of delivery. As a general proposition, a dosage from about 0.5 to about 20 mg/kg body weight, preferably from about 1.0 to about 5.0 mg/kg, will have some therapeutic efficacy. When administered conjointly with other pharmaceutically active agents, even less of the compounds of the invention may be therapeutically effective.

The compounds of the invention can be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation.

VI. EXAMPLE

The following examples are given to illustrate the invention, but should not be considered in limitation of the invention. Examples 1–12 illustrate methods of forming compounds of Formula I. Example 13 illustrates the $\beta_3$-adrenoreceptor selectivity of compounds of the present invention.

Example 1

Preparation of N-[1-(3,5-Dibromo-4-methoxy-benzyl)-6-hydroxy-1,2,3,4-tetrahydro-isoquinolin-7-yl]-methanesulfonamide Hydrochloride

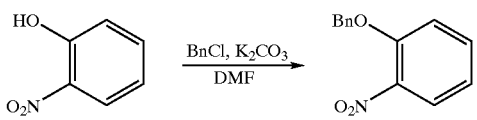

Benzyl-2-nitrophenyl Ether. A mixture of 2-nitrophenol (27.82 g~0.18 mol, Lancaster, contains ca 10% $H_2O$), $K_2CO_3$ (33.15 g, 0.24 mol), and benzyl chloride (30.38 g, 27.6 ml, 0.24 mol) was heated at 100° C. for 1.5 h. The resulting mixture was poured in 1.3 L of water and extracted with $CHCl_3$ tree times, washed twice with 50% brine, dried with $Na_2SO_4$, filtered and concentrated. Distillation in vacuum gave 39.23 g (96%), bp 161–162° C. (~0.1 mm Hg).

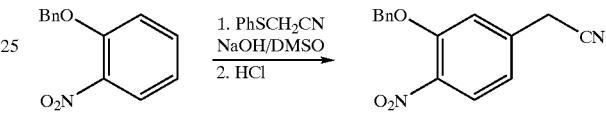

(3-Benzyloxy-4-nitrophenyl)acetonitrile. To a suspension of NaOH (68.44 g 1.71 mol, Aldrich, 20–40 mesh beads) in 171 mL of DMSO a solution of benzyl-2-nitrophenyl ether (39.23 g, 0.171 mol) and (phenylthio)acetonitrile (25.54 g, 0.171 mol, Lancaster) in 171 mL of DMSO was added dropwise for 10 min and stirred at r.t. for another 25 min. A mixture of 430 g of ice and 430 g of conc. HCl was added. The product precipitated and crystallized. The reaction mixture was cooled down in a refrigerator and filtered. The precipitate was dried on air (hood!) and recrystallized from EtOAc-hexanes. Yield 32.03 g (70%), mp 78–80° C.

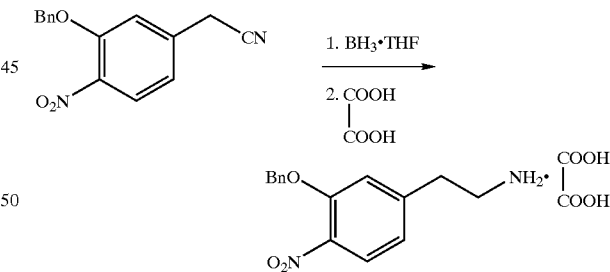

(3-Benzyloxy-4-nitro)phenethylamine Oxalate. 1 M $BH_3$.THF (119 mL, 0.119 mol) was added dropwise to a solution of (3-benzyloxy-4-nitro-phenyl)acetonitrile (32.03 g, 0.119 mol) in 300 mL of anhydrous THF and heated at reflux for 40 min in an argon atmosphere. Cooled down and 100 ml of MeOH was added. The solution was concentrated, basified with 1N NaOH, and extracted three times with $CHCl_3$, washed with water, dried over $Na_2SO_4$, filtered, evaporated. The oily residue was dissolved in MeOH and solution of $(COOH)_2$. $2H_2O$ in MeOH was added. Crystallization was initiated by the addition of ether. Yield 24.44 g (56%), mp 154–156° C.

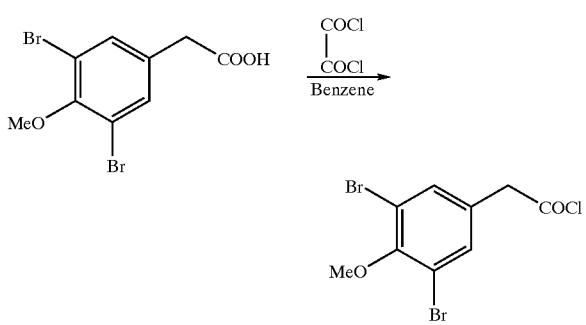

(3,5-Dibromo-4-methoxyphenyl)acetylchloride. A solution of 3,5-dibromo-4-methoxy-phenylacetic acid (30.29 g, 0.093 mol) and oxalyl chloride (118.7 g, 81.6 ml, 0.93 mol) in 300 mL of benzene was refluxed for 6 h. The solution was evaporated with benzene 3 times and dried in vacuum. Yield 100%.

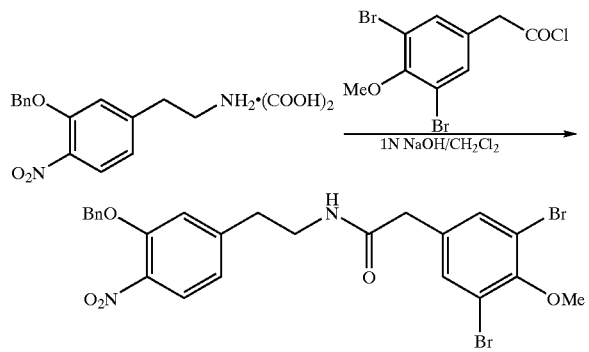

N-(3-Benzyloxy-4-nitrophenethyl)-3,5-dibromo-4-methoxyphenylacetamide. A solution of (3,5-dibromo-4-methoxyphenyl)acetylchloride (25.23 g, 0.0737 mol) in methylene chloride was added to a cold mixture of (3-benzyloxy-4-nitro)phenethylamine oxalate (24.36 g, 0.0672 mol) in 200 mL of $CH_2Cl_2$ and solution of NaOH (40.0 g in 700 mL of water, 1.0 mol) and stirred overnight at r.t. Another portion of acid chloride (2.30 g, 0.00672 mol) in 20 mL of $CH_2Cl_2$ was added and stirred for 1 h. The resulting solution was extracted 3 times with chloroform, washed with water, 1N HCl, water, dried over $Na_2SO_4$. Crystallization from EtOAc-hexanes gave 33.17 g (85%) of the product.

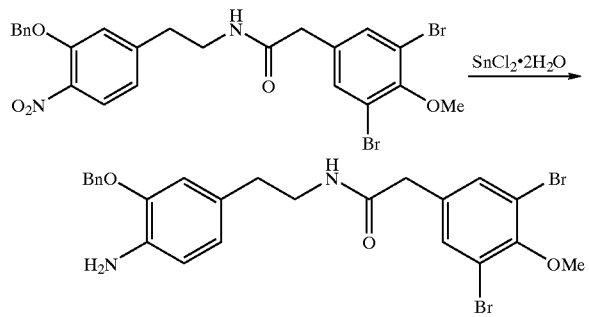

N-[2-(4-amino-3-benzyloxy-phenyl)-ethyl]-2-(3,5-dibromo-4-methoxy-phenyl)-acetamide. A solution of N-(3-Benzyloxy-4-nitrophenethyl)-3,5-dibromo-4-methoxyphenylacetamide (3.49 g, 0.006 mol) and tin (II) chloride dihydrate (16.10 g, 0.071 mol) in a mixture of ethanol (300 mL) and 1.2 N HCl (150 mL) was refluxed for 3h, cooled and concentrated. Tin salts were dissolved in 1N NaOH solution. The reaction mixture was extracted with methylene chloride 3 times. The extracts were dried over $Na_2SO_4$ and concentrated. A residue was crystallized from ethyl acetate-hexanes mixture. Yield 1.57 g (47.4%).

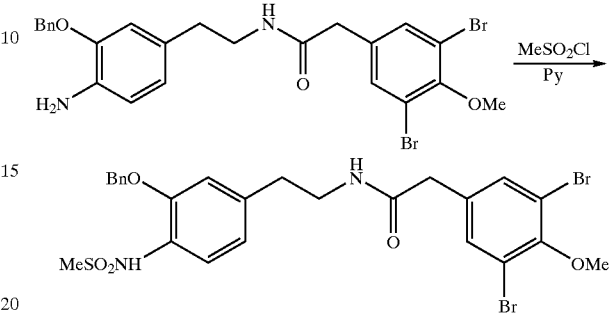

N-[2-(3-benzyloxy-4-methanesulfonylamino-phenyl)-ethyl]-2-(3,5-dibromo-4-methoxy-phenyl)-acetamide. Methanesulfonyl chloride (0.148 g, 0.0013 mol) was added dropwise a solution of N-[2-(4-amino-3-benzyloxy-phenyl)-ethyl]-2-(3,5-dibromo-4-methoxy-phenyl)-acetamide (0.712 g, 0.0013 mol) in 6 mL of pyridine. The reaction mixture was stirred overnight at room temperature, diluted with 10 mL of chloroform, washed with 1N HCl and 1N NaOH, dried over $Na_2SO_4$ and concentrated. A residue was crystallizedfrom ethyl acetate-hexanes mixture. Yield 0.635 g (78%).

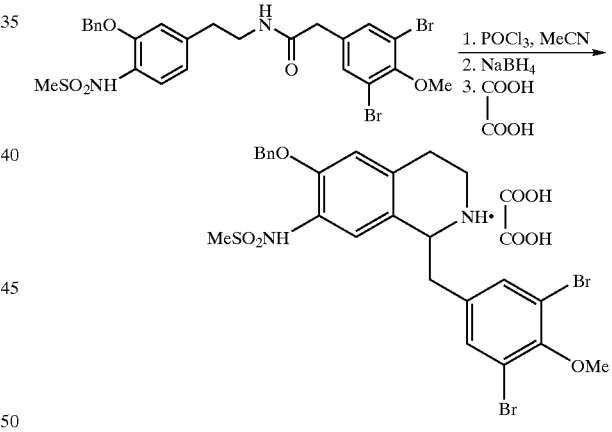

N-[6-benzyloxy-1-(3,5-dibromo-4-methoxy-benzyl)-1,2,3,4-tetrahydroisoquinolin-7-yl]-methanesulfonamide oxalate. A solution of N-[2-(3-benzyloxy-4-methanesulfonylamino-phenyl)-ethyl]-2-(3,5-dibromo-4-methoxy-phenyl)-acetamide (0.457 g, 0.00073 mol) and phosphorus oxychloride (3.29 g, 0.02145 mol) in 20 mL of dry acetonitrile was refluxed for 5h, cooled, concentrated, evaporated with methanol 3 times and finally dissolved in 30 mL of methanol. Sodium borohydride (0.395 g, 0.0104 mol) was added by small portions. The reaction mixture was stirred overnight at room temperature, concentrated, dissolved in chloroform, washed with 1N NaOH, 1N HCl, 1N NaOH, dried over $Na_2SO_4$, concentrated and finally dissolved in methanol. A solution of $(COOH)_2.2H_2O$ in MeOH was added. The product was crystallized from methanol—ethyl ether mixture. Yield 0.381 g (74.55%).

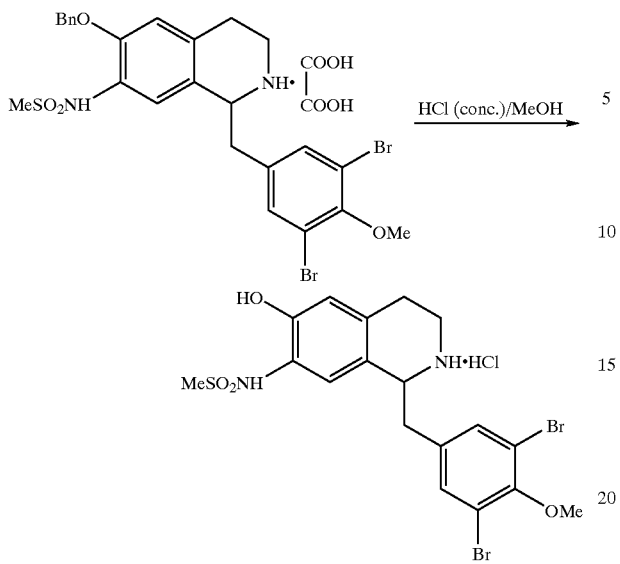

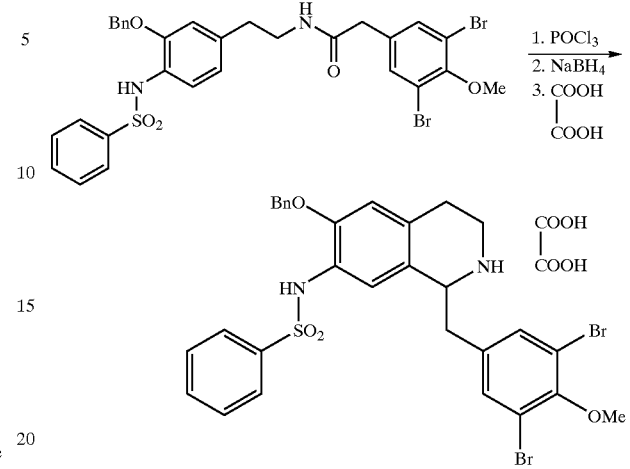

N-[1-(3,5-dibromo-4-methoxy-benzyl)-6-hydroxy-1,2,3,4-tetrahydro-isoquinolin-7-yl]-methanesulfonamide hydrochloride. A solution of N-[6-benzyloxy-1-(3,5-dibromo-4-methoxy-benzyl)-1,2,3,4-tetrahydroisoquinolin-7-yl]-methanesulfonamide oxalate (3.98 g, 0.0057 mol) in a mixture of conc. HCl (50 mL) and methanol (50 mL) was refluxed for 1h, cooled and concentrated. A residue was crystallized from methanol—ethyl ether mixture. Yield 2.75 g (87%), M.p. 244–245° C. (dec.). $^1$H NMR (300 MHz, DMSO) δ 2.9 (s, 3H), 2.95–3.22 (m, 4H), 3.25–3.45 (m, 2H), 3.79 (s, 3H), 4.67 (m, 1H), 6.75 (s, 1H), 7.15 (s, 1H), 7.79 (s, 2H), 8.84 (s, 1H), 9.26 (d, J=12.6 Hz, 2H), 10.18 (s, 1H). Anal. ($C_{18}H_{21}Br_2ClN_2O_4S$) calcd., C 38.83, H 3.80, N 5.03; found C 38.91, N 4.83.

Example 2

Preparation of N-[1-(3,5-Dibromo-4-methoxy-benzyl)-6-hydroxy-1,2,3,4-tetrahydro-isoquinolin-7-yl]-benzenesulfonamide Hydrochloride

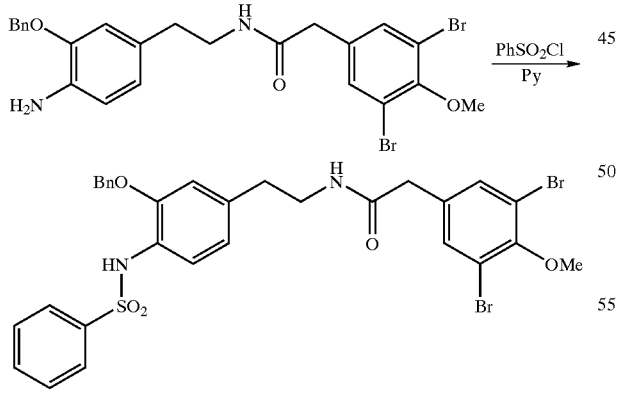

N-[2-(4-benzenesulfonylamino-3-benzyloxy-phenyl)-ethyl]-2-(3,5-dibromo-4-methoxy-phenyl)-acetamide. To a solution of N-[2-(4-amino-3-benzyloxy-phenyl)-ethyl]-2-(3,5-dibromo-4-methoxy-phenyl)-acetamide (0.995 g, 0.00181 mol) and phenylsulfonyl chloride (0.484 g, 0.00274 mol) 40 mL of methylene chloride was added 5 mL of pyridine. The reaction mixture was stirred overnight at room temperature, washed with 1N HCl and 1N NaOH, dried over $Na_2SO_4$ and concentrated. A crystallization from ethyl acetate-hexanes gave an oil. It was solidified under standing. Yield 1.043 g (83%).

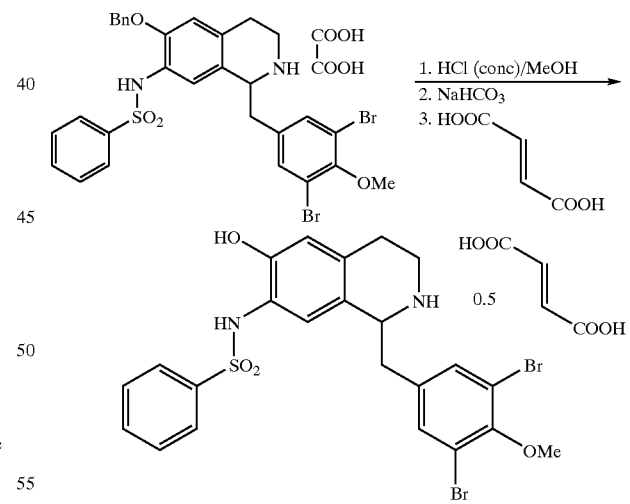

N-[6-benzyloxy-1-(3,5-dibromo-4-methoxy-benzyl)-1,2,3,4-tetrahydro-isoquinolin-7-yl]-benzenesulfonamide oxalate. N-[2-(4-benzenesulfonylamino-3-benzyloxy-phenyl)-ethyl]-2-(3,5-dibromo-4-methoxy-phenyl)-acetamide (0.805 g, 0.00117 mol) and phosphorus oxychloride (4.94 g, 0.0322 mol) in 30 mL of dry acetonitrile was refluxed for 5h, cooled, concentrated, evaporated with methanol 3 times and finally dissolved in 30 mL of methanol. Sodium borohydride (0.654 g, 0.0173 mol) was added by small portions. The reaction mixture was stirred overnight at room temperature, concentrated, dissolved in chloroform, washed with 1N NaOH, 1N HCl and 1N NaOH solutions, dried over $Na_2SO_4$, concentrated and finally dissolved in methanol. A solution of $(COOH)_2 \cdot 2H_2O$ in MeOH was added. Oxalic salt was crystallized from methanol—ethyl ether mixture. Yield 0.551 g (62%).

N-[1-(3,5-dibromo-4-methoxy-benzyl)-6-hydroxy-1,2,3,4-tetrahydro-isoquinolin-7-yl]-benzenesulfonamide hydrochloride. N-[6-benzyloxy-1-(3,5-dibromo-4-methoxy-benzyl)-1,2,3,4-tetrahydro-isoquinolin-7-yl]-benzenesulfonamide oxalate (0.389 g, 0.00051 mol) was neutralized in a mixture 1N NaOH-methylene chloride. A free base was dissolved in a methanol—conc. HCl mixture (35 mL of each). The reaction mixture was refluxed for 1h and evaporated. HCl salt was neutralized with conc. $NaHCO_3$ solution. The product was purified by column chromatography (silica gel, chloroform-methanol—aq. ammonia/100:10:1) and dissolved in methanol, a solution of fumaric acid in methanol was added. A fumaric salt was crystallized from methanol—ethyl ether mixture.

Yield 0.138 g (42%). Mp. 201–203° C. (dec.) $^1$H NMR (300 MHz, DMSO) δ 2.53–2.69 (m, 2H), 2.7–2.89 (m, 2H), 2.9–3.02 (m, 1H), 3.03–3.17 (m, 1H), 3.77 (s, 3H), 4.1–4.28 (m, 1H), 6.44 (s, 1H), 6.47 (s, 1H), 7.01 (s, 1H), 7.35–7.67 (m, 6H), 7.71 (s, 1H), 7.73 (s, 1H).

Example 3

Preparation of N-[1-(3,5-Dibromo-4-methoxy-benzyl)-6-hydroxy-1,2,3,4-tetrahydro-isoquinolin-7-yl]-4-methyl-benzenesulfonamide Hydrochloride

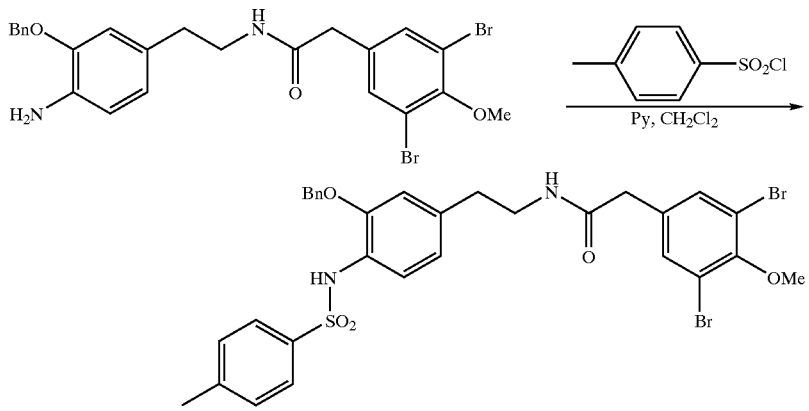

N-{2-[3-benzyloxy-4-(toluene-4-sulfonylamino)-phenyl]-ethyl}-2-(3,5-dibromo-4-methoxy-phenyl)-acetamide. To a solution of N-[2-(4-amino-3-benzyloxy-phenyl)-ethyl]-2-(3,5-dibromo-4-methoxy-phenyl)-acetamide (0.836 g, 0.00152 mol) and p-toluenesulfonyl chloride (0.440 g, 0.00231 mol) in 40 mL of methylene chloride qas added 4 mL of pyridine. The reaction mixture was stirred for 54 h at room temperature, washed with 1N HCl, 1N NaOH solutions, dried over Na$_2$SO$_4$ and evaporated. A residue was crystallized from ethyl acetate-hexanes mixture. Yield 0.933 g (87%).

N-[6-benzyloxy-1-(3,5-dibromo-4-methoxy-benzyl)-1,2,3,4-tetrahydro-isoquinolin-7-yl]-4-methyl-benzenesulfonamide oxalate. To a solution of N-{2-[3-benzyloxy-4-(toluene-4-sulfonylamino)-phenyl]-ethyl}-2-(3,5-dibromo-4-methoxy-phenyl)-acetamide (0.41 g, 0.000584 mol) in 15 mL of acetonitrile phosphorus oxychloride (2.47 g, 0.0161 mol) was added. The reaction mixture was refluxed for 5 h. The residue after concentration was evaporated 3 times with MeOH, dissolved in 20 mL of MeOH, cooled with an ice bath, and NaBH$_4$ (0.305 g, 0.00806 mol) was added by small portions. The reaction mixture was stirred overnight at room temperature, concentrated, dissolved in chloroform, washed with 1N NaOH, dried over Na$_2$SO$_4$, filtered, and concentrated. The residue was dissolved in methanol, a solution of (COOH)$_2$.2H$_2$O in methanol was added. Oxalic salt was crystallized from methanol—ethyl ether mixture. Yield 0.253 g (63%).

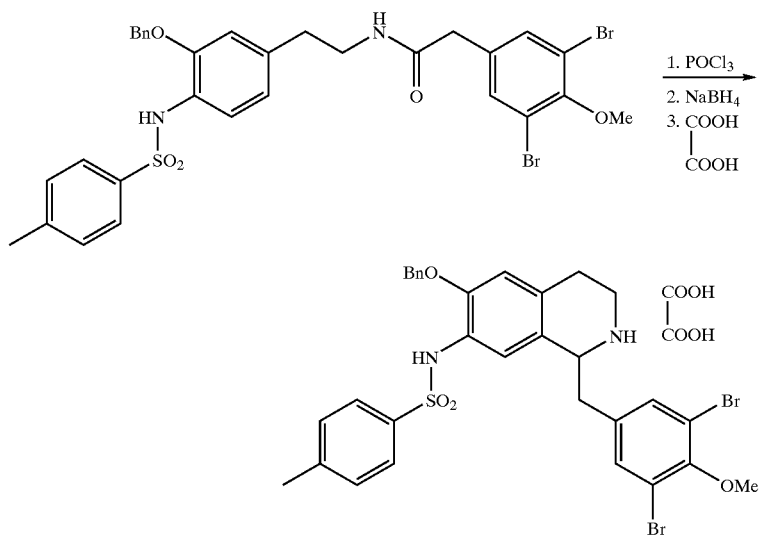

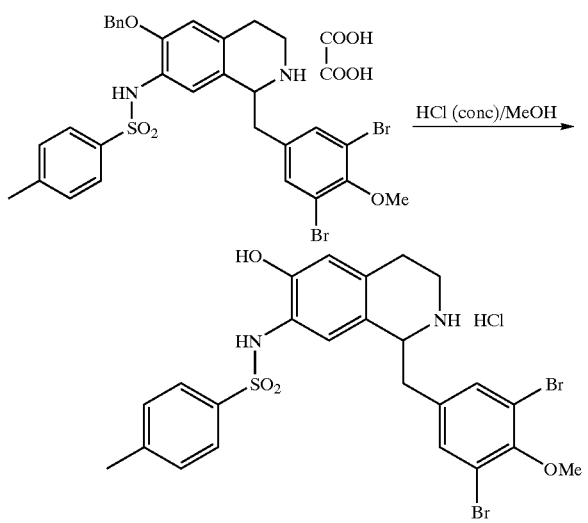

N-[1-(3,5-dibromo-4-methoxy-benzyl)-6-hydroxy-1,2,3,4-tetrahydro-isoquinolin-7-yl]-4-methyl-benzenesulfonamide hydrochloride. N-[6-benzyloxy-1-(3,5-dibromo-4-methoxy-benzyl)-1,2,3,4-tetrahydro-isoquinolin-7-yl]-4-methyl-benzenesulfonamide oxalate (0.48 g, 0.00062 mol) was neutralized in a mixture 1N NaOH-methylene chloride. A free base was dissolved in a methanol—conc. HCl mixture (20 mL of each). The reaction mixture was refluxed for 1 h and evaporated. A residue was crystallized from methanol—ethyl ether mixture.

Yield 0.192 g (49%). Mp. 230–232° C. (dec.) $^1$H NMR (300 MHz, DMSO) δ 2.31 (s, 3H), 2.65–3.4 (m, 6H), 3.8 (s, 3H), 4.55–4.8 (m, 1H), 6.56 (s, 1H), 7.07 (s, 1H), 7.28 (d, J=8.1 Hz, 2H), 7.59 (d, J=8.2 Hz, 2H), 7.76 (s, 2H), 9.12–9.4 (m, 3H), 9.84 (s, 1H).

Example 4

Preparation of N-[1-(3,5-Dibromo-4-methoxy-benzyl)-6-hydroxy-1,2,3,4-tetrahydro-isoquinolin-7-yl]-4-methoxy-benzenesulfonamide Hydrochloride

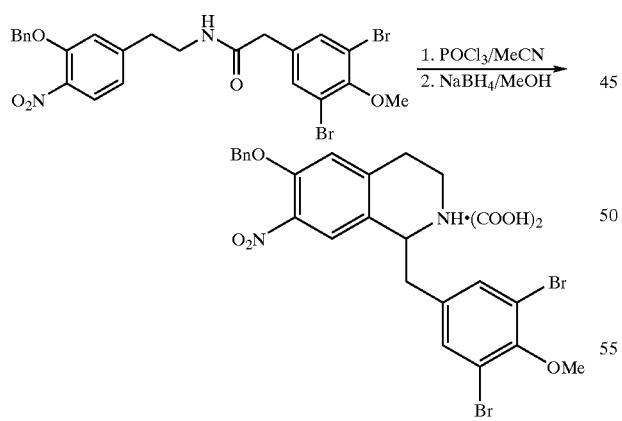

6-Benzyloxy-1-(3,5-dibromo-4-methoxybenzyl)-7-nitro-1,2,3,4-tetrahydro-isoquinoline oxalate. To a solution of N-(3-Benzyloxy-4-nitrophenethyl)-3,5-dibromo-4-methoxyphenyl-acetamide (23.13 g 0.04 mol) in 400 mL of acetonitrile 40 mL of POCl$_3$ was added and refluxed for 5 h. The residue after concentration was evaporated 3 times with MeOH, dissolved in 400 mL of MeOH, cooled with an ice bath, and NaBH$_4$ (37.83 g, 0.40 mol) was added by small portions and stirred for additional 2 h at room temperature. The reaction mixture was concentrated, CHCl$_3$ added and washed with 10% solution of NaOH and 50% brine twice, then with water, dried over Na$_2$SO$_4$, filtered, and concentrated. The residue was dissolved in CHCl$_3$ and a solution of (COOH)$_2$.2H$_2$O in MeOH was added. Crystallization started immediately, some ether was added. Yield 19.43 g (74%), mp 169–171° C.

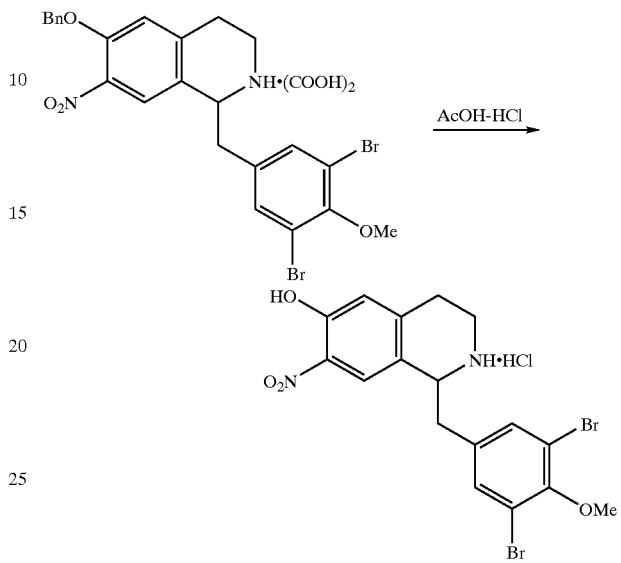

1-(3,5-dibromo-4-methoxybenzyl)-7-nitro-1,2,3,4-tetrahydroisoquinolin-6-ol hydrochloride. A solution of 6-benzyloxy-1-(3,5-dibromo-4-methoxybenzyl)-7-nitro-1,2,3,4-tetrahydroisoquinoline oxalate (13.05 g, 0.02 mol) in 250 mL of acetic acid and 250 mL of conc. HCl was refluxed for 1 h, solvents evaporated to dryness and the residue was recrystallized from MeOH-ether (first dissolved in 500 mL of MeOH and concentrated in a stream of argon). Yield 9.04 g (89%).

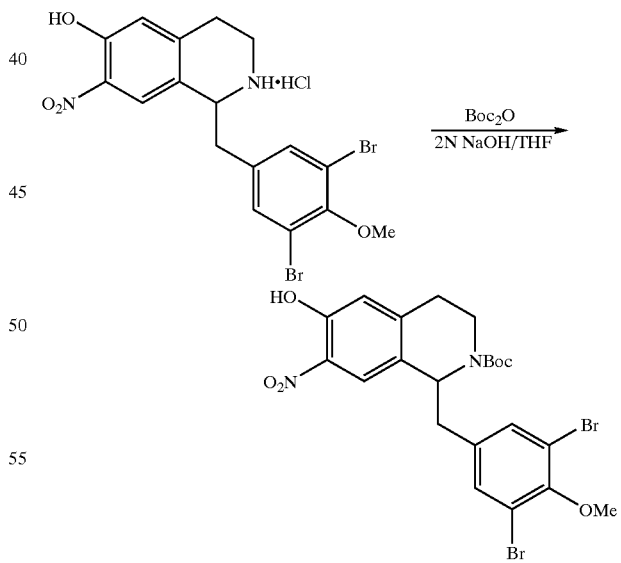

1-(3,5-dibromo-4-methoxybenzyl)-6-hydroxy-7-nitro-1,2,3,4-tetrahydro-isoquinoline-2-carboxylic acid tert-butyl ester. A solution of 1-(3,5-dibromo-4-methbxybenzyl)-7-nitro-1,2,3,4-tetrahydroisoquinolin-6-ol hydrochloride (1.017 g, 0.002 mol), 2N NaOH (10 mL) and Boc$_2$O (0.654 g, 0.003 mol) in 40 mL of THF was stirred for 1.5 h at room temperature. A solution of Boc$_2$O (0.1 g, 0.00045 mol) in 3 mL of THF was added again. The reaction mixture was stirred overnight at room temperature. A solution of Boc$_2$O (0.1 g, 0.00045 mol) in 3 mL of THF was added additionally. The reaction mixture was stirred for 1 h and concentrated. Satur. NaHCO$_3$ solution, brine, water were added. The resulting mixture was extracted 3 times with chloroform. The extracts were dried over Na$_2$SO$_4$ and evaporated to dryness. The residue was used in the next step without additional purification.

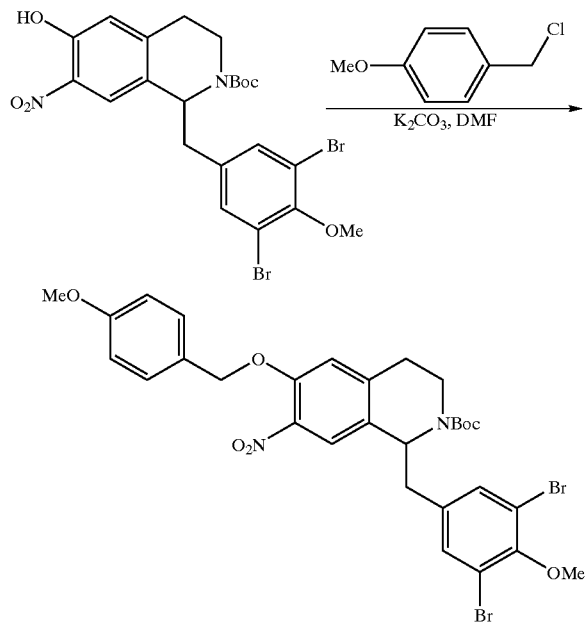

1-(3,5-dibromo-4-methoxybenzyl)-6-(4-methoxy-benzyloxy)-7-nitro-1,2,3,4-tetrahydro-isoquinoline-2-carboxylic acid tert-butyl ester. A mixture of 1-(3,5-dibromo-4-methoxy-benzyl)-6-hydroxy-7-nitro-1,2,3,4-tetrahydroisoquinoline-2-carboxylic acid tert-butyl ester (0.002 mol), K$_2$CO$_3$ (0.331 g, 0.0024 mol) and 4-methoxybenzyl chloride (0.376 g, 0.0024 mol) in 10 mL of DMF was heated for 4 h at 100° C. 0.17 g (0.00109 mol) of 4-methoxybenzyl chloride was added additionally. The reaction mixture was heated for 5 h at 100° C., cooled, poured in water, cooled, filtered and dried in vacuum. The residue was dissolved in ethyl acetate and filtered through silica gel. The solution was concentrated. The residue was crystallized from chloroform-hexanes mixture. Yield 0.96 g (72%).

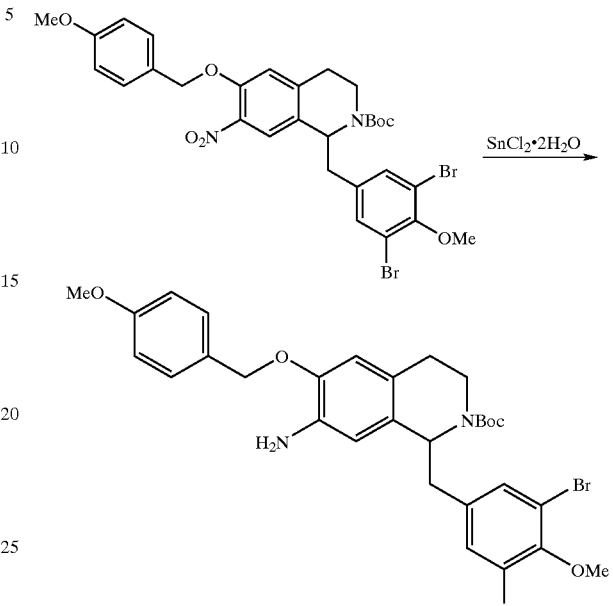

1-(3,5-dibromo-4-methoxybenzyl)-6-(4-methoxy-benzyloxy)-7-amino-1,2,3,4-tetra-hydro-isoquinoline-2-carboxylic acid tert-butyl ester. To a solution of 1-(3,5-dibromo-4-methoxybenzyl)-6-(4-methoxy-benzyloxy)-7-nitro-1,2,3,4-tetrahydro-isoquinoline-2-carboxylic acid tert-butyl ester (8.31 g, 0.012 mol) in 120 mL of ethyl acetate and 12 mL of pyridine was added powder tin (II) chloride dihydrate (27.08 g, 0.12 mol). The reaction mixture was stirred for 5 h at 55° C., cooled and filtered. The filtrate was washed 2 times with 1N NaOH. Water phase was extracted with chloroform. The extracts and ethyl acetate solution were combined, dried over Na$_2$SO$_4$ and concentrated. The product was purified by column chromatography (silica gel, ethyl acetate-hexanes mixture (1:4)), evaporated with ethyl ether and dried in vacuum. Yield 4.864 g (61%).

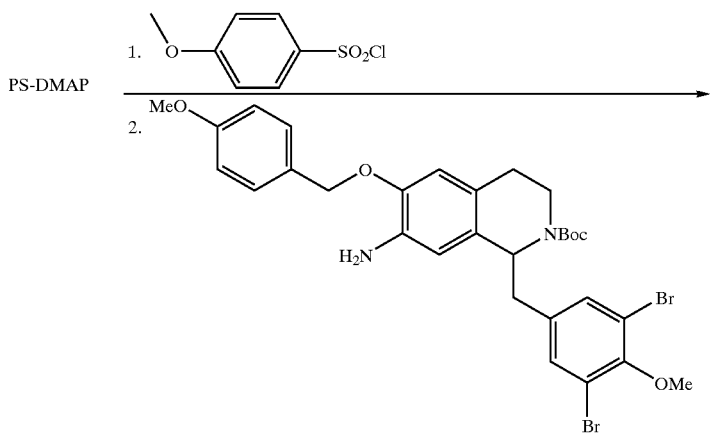

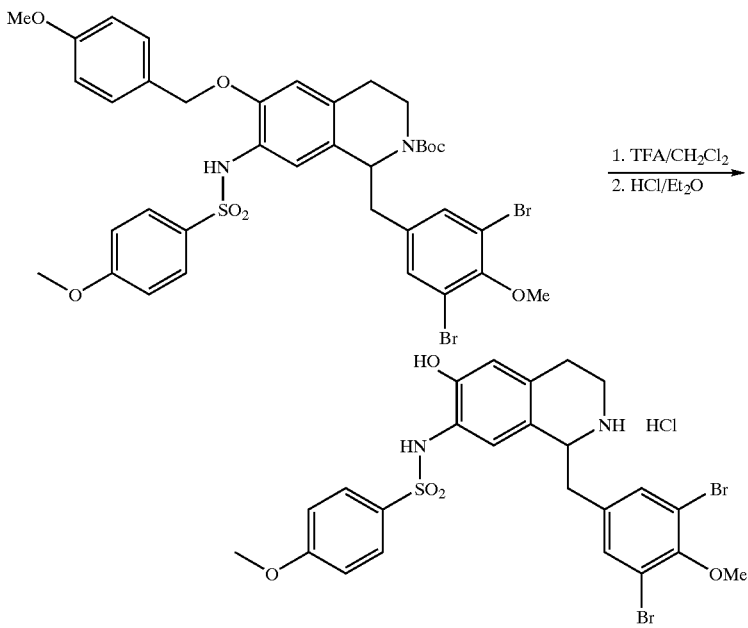

N-[1-(3,5-dibromo-4-methoxy-benzyl)-6-hydroxy-1,2,3,4-tetrahydro-isoquinolin-7-yl]-4-methoxy-benzenesulfonamide hydrochloride. PS-DMAP resin (Aldrich) (7.5 g, 0.0002 mol of DMAP is available) was washed with methylene chloride 3 times, a solvent was sucked and finally 10 ml of methylene chloride was added followed by 4-methoxy-phenylsulfonyl chloride (0.62 g, 0.003 mol). The mixture was agitated for 4 h, washed with methylene chloride 10 times, finally 10 ml of methylene chloride was added followed by 1-(3,5-dibromo-4-methoxybenzyl)-6-(4-methoxy-benzyloxy)-7-amino-1,2,3,4-tetrahydroisoquinoline-2-carboxylic acid tert-butyl ester (0.199 g, 0.003 mol). The reaction mixture was agitated for 2 days and filtered. A product was purified by column chromatography (ethyl acetate-hexanes/1:2) and dissolved in a mixture of TFA and methylene chloride (5 mL of each). The reaction mixture was stirred for 2.5 h at room temperature and evaporated. The product was purified by column chromatography (chloroform-methanol—aq. ammonia/100:10:1). HCl salt was prepared and crystallized from methanol—ethyl ether mixture. Yield 0.140 g (72%). Mp. 226–228° C. (dec.) $^1$H NMR (300 MHz, DMSO) δ 2.68–2.86 (m, 1H), 2.87–3.24 (m, 4H), 3.2–3.46 (m, 1H), 3.76 (s, 3H), 3.8 (s, 3H), 4.55–4.78 (m, 1H), 6.56 (s, 1H), 7.0 (d, J=8.6 Hz, 2H), 7.07 (s, 1H), 7.63 (d, J=8.6 Hz, 2H), 7.77 (s, 2H), 9.19 (s, 1H), 9.27 (s, 2H), 9.83 (s, 1H). Anal. ($C_{24}H_{24}Br_2N_2O_5S$ HCl) calcd., C 44.43, H 3.88, N 4.32; found C 44.30, H 3.91, N 4.19.

Example 5

Preparation of N-[1-(3,5-dibromo-4-methoxy-benzyl)-6-hydroxy-1 2,3,4-tetrahydro-isoquinolin-7-yl]-4-trifluoromethoxy-benzenesulfonamide Hydrochloride

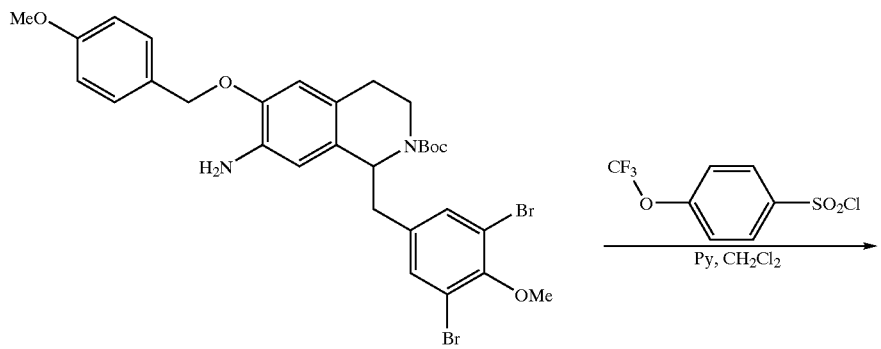

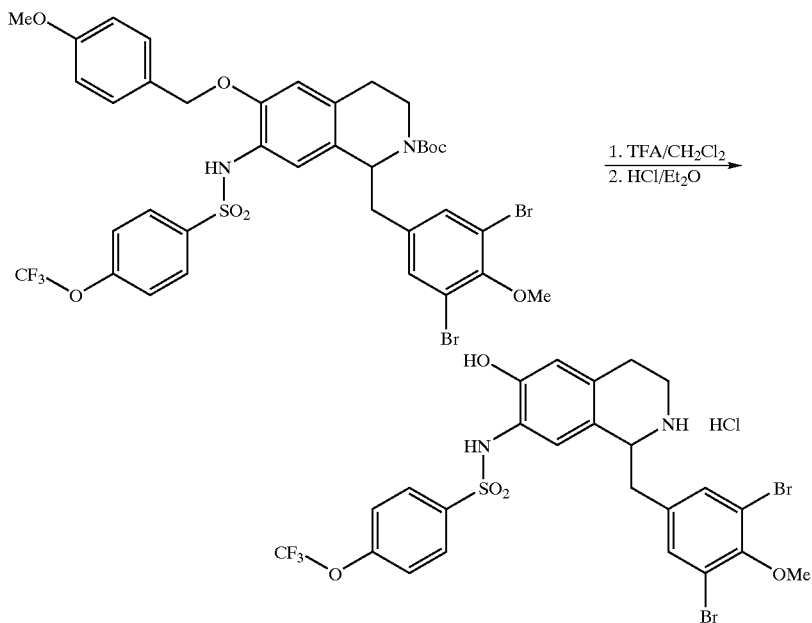

N-[1-(3,5-dibromo-4-methoxy-benzyl)-6-hydroxy-1,2,3,4-tetrahydro-isoquinolin-7-yl]-4-trifluoromethoxy-benzenesulfonamide hydrochloride. To a solution of 1-(3,5-dibromo-4-methoxybenzyl)-6-(4-methoxy-benzyloxy)-7-amino-1,2,3,4-tetrahydro-isoquinoline-2-carboxylic acid tert-butyl ester (0.203 g, 0.000306 mol) and 1 mL pyridine in 3 mL of methylene chloride was added a solution 4-trifluoromethoxyphenyl-sulfonyl chloride (0.091 g, 0.00035 mol) in 1 mL of methylene chloride. The reaction mixture was stirred for 6 days at room temperature, washed with 1N NaOH (3 times) and water, dried over $Na_2SO_4$ and evaporated. A product was purified by column chromatography (silica gel, ethyl acetate-hexanes/1:3) and dissolved in a mixture of TFA and methylene chloride (3 mL of each). The reaction mixture was stirred for 3 h at room temperature and evaporated. The product was purified by column chromatography (silica gel, chloroform-methanol—aq. ammonia/100:10:1). HCl salt was prepared and crystallized from methanol—ethyl ether mixture. Yield 0.173 g (80%). Mp. 212–215° C. $^1$H NMR (300 MHz, DMSO) δ 2.7–2.88 (m, 1H), 2.9–3.4 (m, 5H), 3.8 (s, 3H), 4.55–4.8 (m, 1H), 6.57 (s, 1H), 7.1 (s, 1H), 7.1 7.51 (d, J=8.2 Hz, 2H), 7.77 (s, 2H), 7.83 (d, J=8.77 Hz, 2H), 9.21 (s, 2H), 9.62 (s, 1H).

Example 6

Preparation of N-[1-(3,5-Dibromo-4-methoxy-benzyl)-6-hydroxy-1,2,3,4-tetrahydro-isoguinolin-7-yl]-4-trifluoromethyl-benzenesulfonamide Hydrochloride

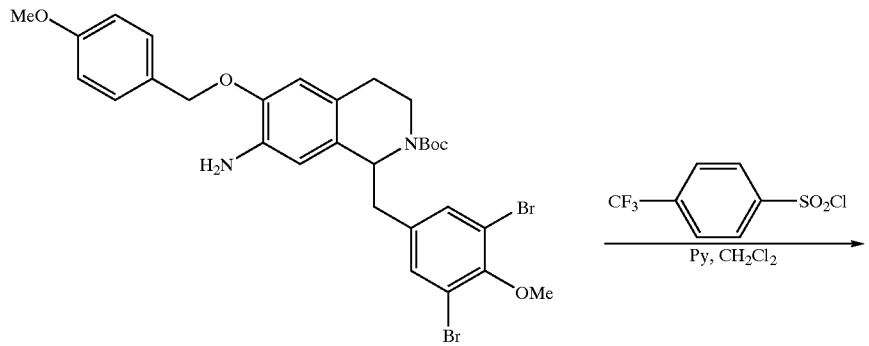

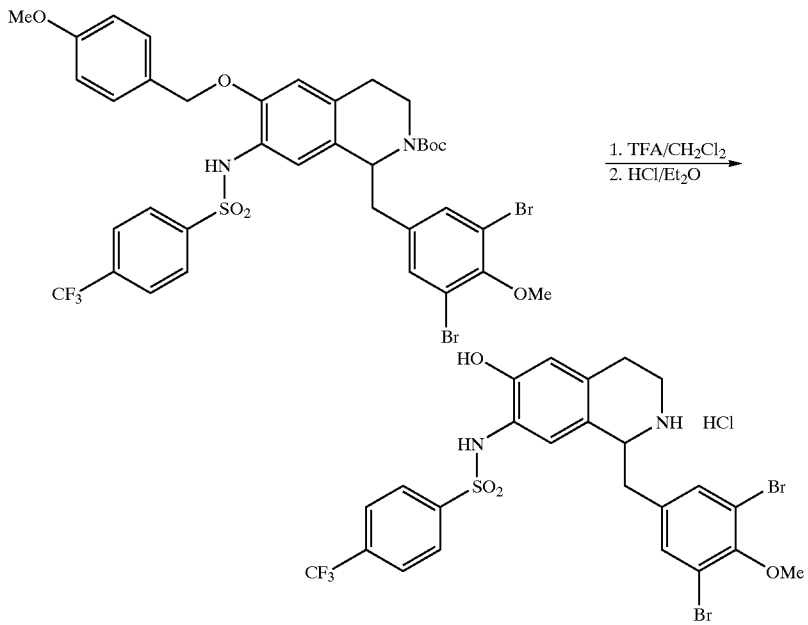

N-[1-(3,5-dibromo-4-methoxy-benzyl)-6-hydroxy-1,2,3,4-tetrahydro-isoquinolin-7-yl]-4-trifluoromethyl-benzenesulfonamide hydrochloride. To a solution of 1-(3,5-dibromo-4-methoxybenzyl)-6-(4-methoxy-benzyloxy)-7-amino-1,2,3,4-tetrahydro-isoquinoline-2-carboxylic acid tert-butyl ester (0.202 g, 0.000305 mol) and 1 mL pyridine in 4 mL of methylene chloride was added a solution of 4-trifluoromethylphenylsulfonyl chloride (0.082 g, 0.000335 mol) in 1 mL of methylene chloride. The reaction mixture was stirred overnight at room temperature, washed with 1N NaOH and water (3 times), dried over $Na_2SO_4$ and evaporated. A product was purified by column chromatography (silica gel, ethyl acetate-hexanes/1:3) and dissolved in a mixture of TFA and methylene chloride (3 mL of each). The reaction mixture was stirred for 3 h at room temperature and evaporated. The product was purified by column chromatography (silica gel, chloroform-methanol—aq. ammonia/100:10:1). HCl salt was prepared and crystallized from methanol-ethyl ether mixture. Yield 0.167 g, (80%). Mp. 176–179° C. $^1$H NMR (300 MHz, methanol-$d_4$) δ 2.75–3.1 (m, 3H), 3.2–3.48 (m, 3H), 3.79 (s, 3H), 4.67 (t, J=7.4 Hz 1H), 6.48 (s, 1H), 7.05 (s, 1H), 7.52 (s, 2H), 7.66 (d, J=8.3 Hz, 2H), 7.79 (d, J=8.13 Hz, 2H).

Example 7

Preparation of N-[1-(3,5-Dibromo-4-methoxybenzyl)-6-hydroxy-1,2,3,4-tetrahydroisoiuinolin-7-yl]-4-fluoro-benzenesulfonamide Fumarate

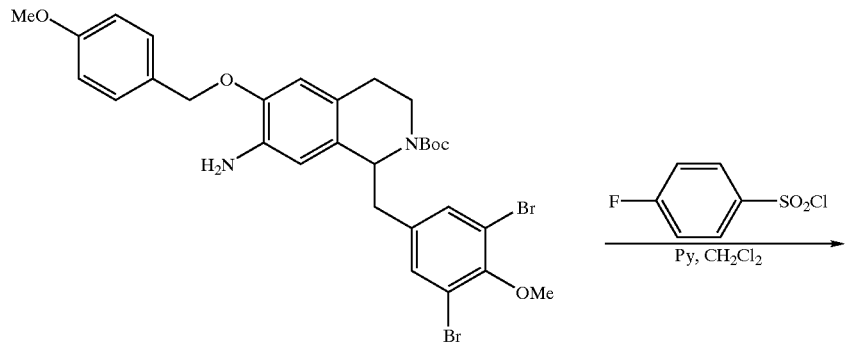

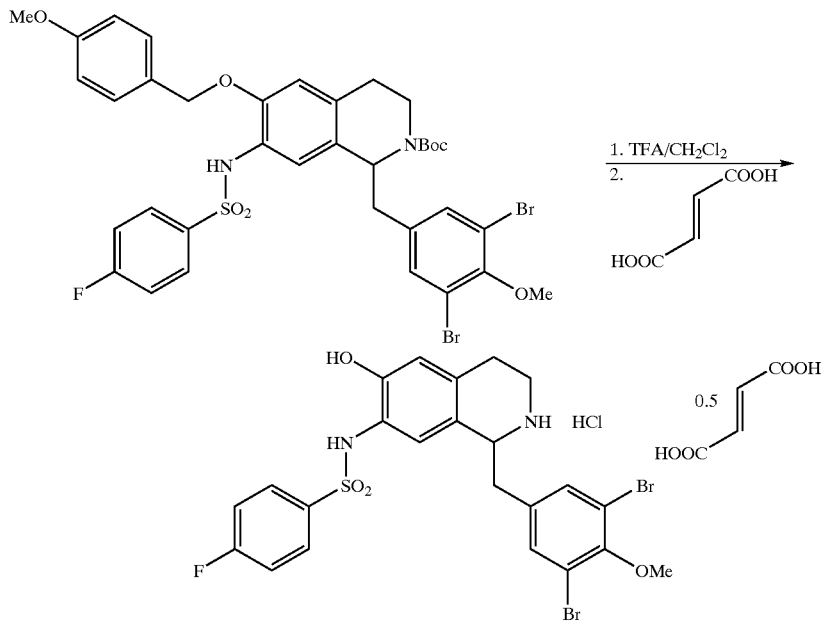

N-[1-(3,5-dibromo-4-methoxybenzyl)-6-hydroxy-1,2,3,4-tetrahydroisoquinolin-7-yl]-4-fluoro-benzenesulfonamide fumarate. To a solution of 1-(3,5-dibromo-4-methoxybenzyl)-6-(4-methoxy-benzyloxy)-7-amino-1,2,3,4-tetrahydroisoquinoline-2-carboxylic acid tert-butyl ester (0.530 g, 0.0008 mol) in 10 mL of methylene chloride and 2 mL of pyridine was added a solution of 4-fluoro-benzenesulfonyl chloride in 4 mL of methylene chloride. The reaction mixture was stirred for 3 h at room temperature, diluted with chloroform, washed with 2N NaOH-brine mixture (3 times), water, brine, dried over $Na_2SO_4$ and evaporated. A residue was dissolved in a mixture of 5 mL of TFA and 5 mL methylene chloride. The reaction mixture was stirred overnight at room temperature and evaporated. The product was purified by column chromatography (silica gel, $CHCl_3$—MeOH—$NH_4OH$ mixture (200:10:2)), dissolved in methanol. The fumaric acid salt was prepared by adding fumaric acid solution in MeOH and crystallized from methanol—ethyl ether mixture. Yield 0.143 g (27%), M.p. 209–211° C. (dec.). $^1$H NMR (300 MHz, DMSO) δ 2.51–2.71 (m, 2H), 2.72–2.92 (m, 2H), 2.94–3.18 (m, 2H), 3.78 (s, 3H), 4.19 (m, 1H), 6.44 (s, 1H), 6.48 (s, 1H), 7.03 (s, 1H), 7.27–7.38 (m, 2H), 7.61 (s, 2H), 7.71–7.8 (m, 2H), 8.78 (s (broad), 1H); Anal. ($C_{25}H_{23}Br_2FN_2O_6S$) calcd., C 45.61, H 3.52, N 4.26; found C 45.51, H 3.43, N 4.13.

Example 8

Preparation of Ethanesulfonic Acid [1-(3,5-Dibromo-4-methoxy-benzyl)-6-hydroxy-1,2,3,4-tetrahydro-isoquinolin-7-yl]-amide Hydrochloride

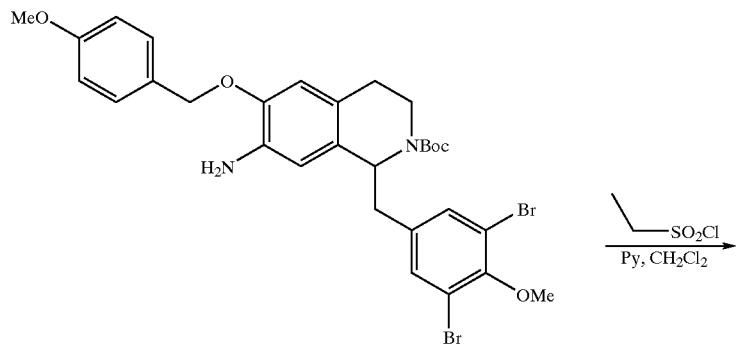

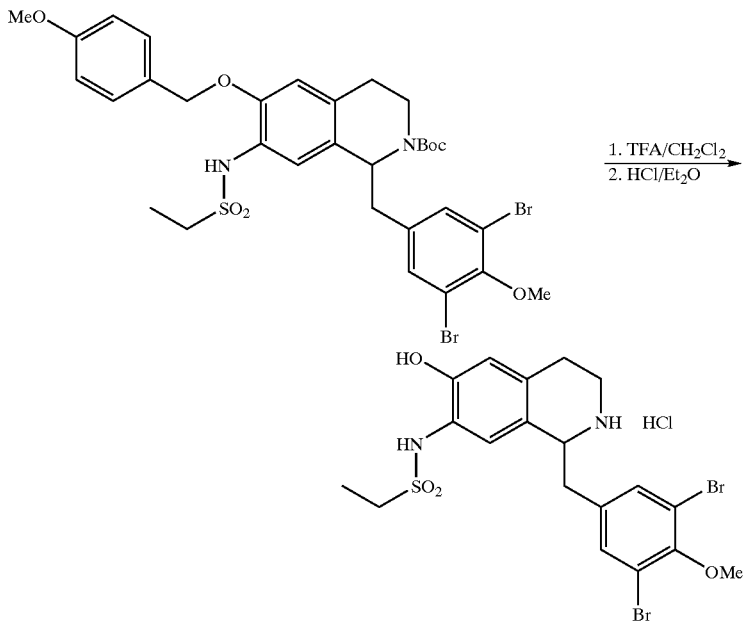

Ethanesulfonic acid [1-(3,5-dibromo-4-methoxy-benzyl)-6-hydroxy-1,2,3,4-tetrahydro-isoquinolin-7-yl]-amide hydrochloride. To a solution of 1-(3,5-dibromo-4-methoxybenzyl)-6-(4-methoxy-benzyloxy)-7-amino-1,2,3,4-tetrahydroisoquinoline-2-carboxylic acid tert-butyl ester (0.404 g, 0.00061 mol) and 1.6 mL of pyridine in 6 mL of $CH_2Cl_2$ was added 0.07 mL of ethanesulfonyl chloride. The reaction mixture was stirred overnight at room temperature, washed with 1N NaOH solution and evaporated. A residue was dissolved in a mixture TFA—methylene chloride (8 mL of each). The reaction mixture was stirred for 1 h at room temperature and evaporated. The product was purified by column chromatography (chloroform-methanol—aq. ammonia/100:10:1) twice. HCl salt was prepared and crystallized from methanol—ethyl ether mixture. Yield 0.256 g (74%). Mp. 240–242° C. (dec). $^1$H NMR (300 MHz, DMSO) δ 1.24 (t, J=7.3 Hz, 3H), 2.77–3.23 (m, 7H), 3.24–3.4 (m, 1H), 3.8 (s, 3H), 4.6–4.82 (m, 1H), 6.75 (s, 1H), 7.13 (s, 1H), 7.78 (s, 2H), 8.78 (s, 1H), 9.15–9.5 (m, 2H), 10.18 (s, 1H). Fumaric acid salt: Mp. 229–231° C. (dec). $^1$H NMR (300 MHz, DMSO) δ 2.56–2.77 (m, 2H), 2.78–3.02 (m, 4H), 3.03–3.22 (m, 2H), 3.77 (s, 3H), 4.19–4.33 (m, 1H), 6.48 (s, 1H), 6.6 (s, 1H), 7.1 (s, 1H), 7.64 (s, 2H), 8–10 (broad, 2H).

Example 9

Preparation of N-[1-(3,5-Dibromo-4-methoxy-benzyl)-6-hydroxy-1,2,3,4-tetrahydro-isoquinolin-7-yl]-C-phenyl-methanesulfonamide Hydrochloride

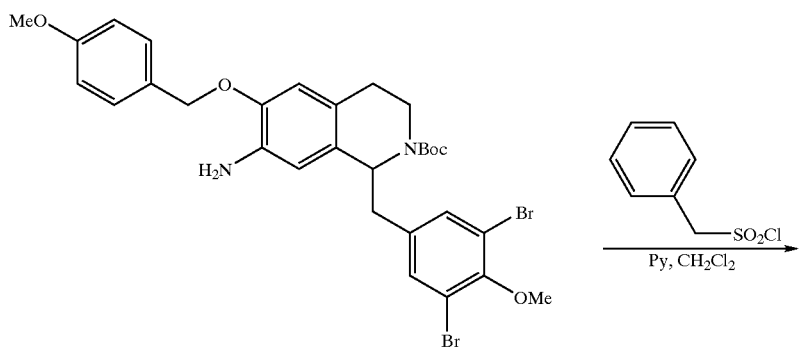

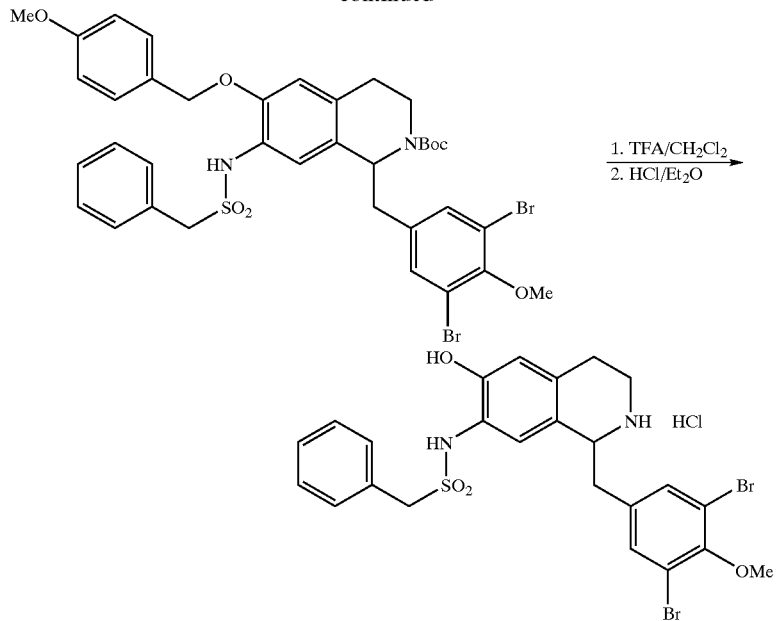

N-[1-(3,5-dibromo-4-methoxy-benzyl)-6-hydroxy-1,2,3,4-tetrahydro-isoquinolin-7-yl]-C-phenyl-methanesulfonamide hydrochloride. To a solution of 1-(3,5-dibromo-4-methoxybenzyl)-6-(4-methoxy-benzyloxy)-7-amino-1,2,3,4-tetrahydroiso-quinoline-2-carboxylic acid tert-butyl ester (0.205 g, 0.000309 mol) and 1 mL of pyridine in 3 mL methylene chloride was added a solution of α-toluenesulfonyl chloride (0.065 g, 0.00034 mol) in 1 mL of methylene chloride The reaction mixture was stirred overnight at room temperature. A solution of 0.039 g of α-toluenesulfonyl chloride in 1 mL of methylene chloride was added. The reaction mixture was stirred overnight at room temperature. A solution of 0.035 g of α-toluenesulfonyl chloride in 1 mL of methylene chloride was added. The reaction mixture was stirred overnight at room temperature, washed with 1N NaOH (3 times) and water, dried over $Na_2SO_4$ and evaporated. A product was purified by column chromatography (ethyl acetate—hexanes/1:2) and dissolved in a mixture of TFA and methylene chloride (3 mL each). The reaction mixture was stirred for 3 h at room temperature and evaporated. The product was purified by column chromatography (silica gel, chloroform-methanol—aq. ammonia/100:10:1). HCl salt was prepared and crystallized from methanol—ethyl ether mixture. Yield 0.121 g (62%). Mp. 243–244° C. $^1$H NMR (300 MHz, DMSO) δ 2.75–2.94 (m, 1H), 2.98–3.21 (m, 3H), 3.23–3.43 (m, 2H), 3.79 (s, 3H), 4.38 (s, 2H), 4.6–4.77 (m, 1H), 6.77 (s, 1H), 7.1 (s, 1H), 7.3–7.42 (m, 5H), 7.8 (s, 2H), 8.76 (s, 1H), 9.1–9.5 (m, 2H), 10.27 (s, 1H).

Example 10

Preparation of 2-phenyl-ethenesulfonic acid [1-(3,5-dibromo-4-methoxy-benzyl)-6-hydroxy-1,2,3,4-tetrahydro-isoquinolin-7-yl]-amide Hydrochloride

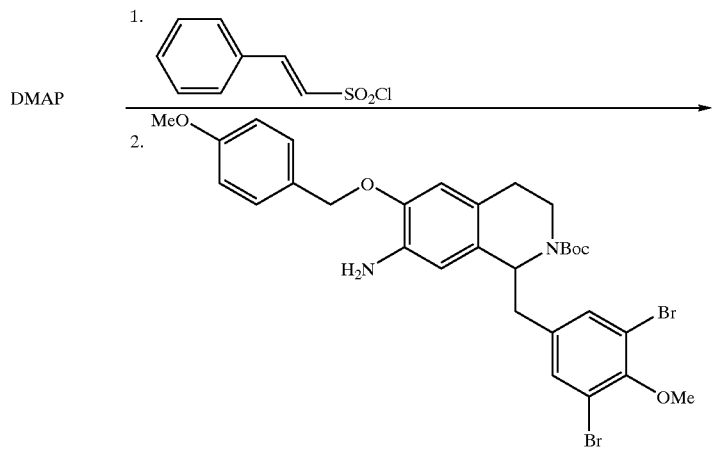

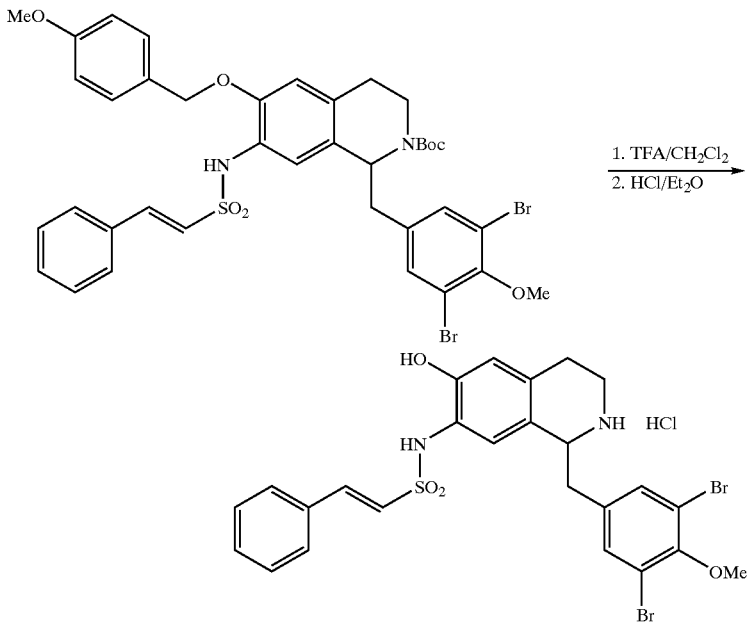

2-phenyl-ethenesulfonic acid [1-(3,5-dibromo-4-methoxy-benzyl)-6-hydroxy-1,2,3,4-tetrahydroisoquinolin-7-yl]-amide hydrochloride. To a solution of DMAP (0.086 g, 0.000704 mol) in 1 mL of methylene chloride was added a solution of trans-α-styrenesulfonyl chloride (0.07 g, 0.000345 mol) in 2 mL of methylene chloride. A reaction mixture was stirred for 10 min at room temperature. A solution of 1-(3,5-dibromo-4-methoxybenzyl)-6-(4-methoxy-benzyloxy)-7-amino-1,2,3,4-tetrahydroisoquinoline-2-carboxylic acid tert-butyl ester (0.209 g, 0.000316 mol) in 2 mL of $CH_2Cl_2$ was added. The reaction mixture was stirred overnight at room temperature. 0.037 g of trans-β-styrenesultonyl chloride was added. A stirring was repeated overnight at room temperature. 0.041 g of trans-β-styrenesulfonyl chloride was added. A stirring was repeated overnight at room temperature. The reaction mixture was washed with 1N NaOH (3 times) and water, dried over $Na_2SO_4$ and evaporated. A purification was carried out by column chromatography (silica gel, ethyl acetate-hexanes/1:2). A product was dissolved in a mixture TFA—$CH_2Cl_2$ (3 mL of each). The reaction mixture was stirred for 3 h at room temperature and evaporated. The product was purified by column chromatography (chloroform-methanol—aq. ammonia/100:10:1). HCl salt was prepared and crystallized from methanol—ethyl ether mixture. Yield 0. 056 g (28%). Mp. 249–250° C. $^1H$ NMR (300 MHz, DMSO) δ 2.73–2.88 (m, 1H), 2.92–3.2 (m, 3H), 3.21–3.4 (m, 2H), 3.81 (s, 3H), 4.6–4.77 (m, 1H), 6.68 (s, 1H), 7.14 (d, J=15.5 Hz, 1H), 7.22 (s, 1H), 7.3 (d, J=15.5 Hz, 1H), 7.35–7.43 (m, 3H), 7.57–7.67 (m, 2H), 7.78 (s, 2H), 9.07 (s, 1H), 9.22 (s, 2H), 10.12 (s, 1H).

Example 11
Preparation of N-[1-(3,4-dichloro-benzyl)-6-hydroxy-1,2,3,4-tetrahydro-isoguinolin-7-yl]-methanesulfonamide Hydrochloride

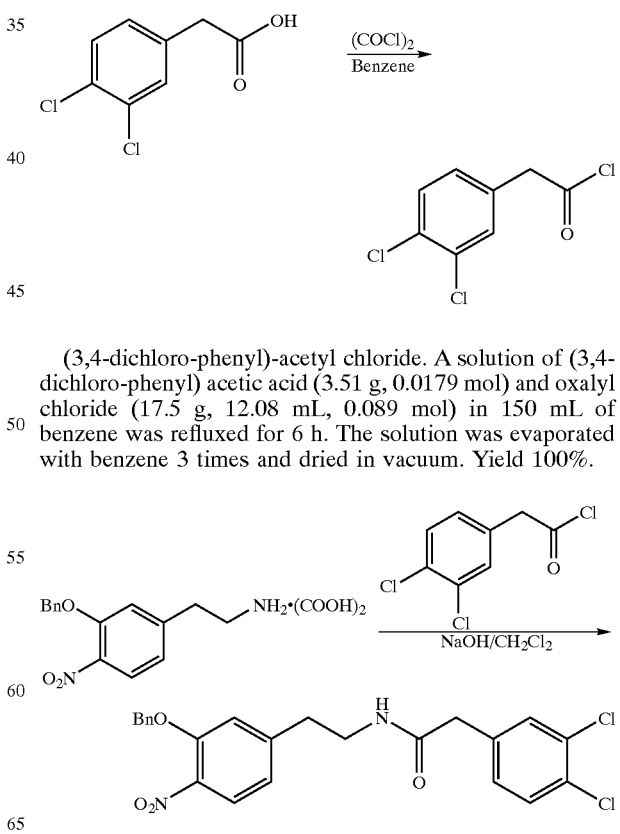

(3,4-dichloro-phenyl)-acetyl chloride. A solution of (3,4-dichloro-phenyl) acetic acid (3.51 g, 0.0179 mol) and oxalyl chloride (17.5 g, 12.08 mL, 0.089 mol) in 150 mL of benzene was refluxed for 6 h. The solution was evaporated with benzene 3 times and dried in vacuum. Yield 100%.

N-[2-(3-benzyloxy-4-nitro-phenyl)-ethyl]-2-(3,4-dichloro-phenyl)-acetamide. A solution of (3,4-dichlorophenyl)-acetyl chloride (3.84 g, 0.0179 mol) in CH$_2$Cl$_2$ was added to a cold mixture of (3-benzyloxy-4-nitro)-phenethylamine oxalate (5 g, 0.0139 mol) in 200 mL of CH$_2$Cl$_2$ and solution of NaOH (8.23 g in 100 mL of water, 0.20 mol) and stirred overnight at room temperature. The resulting solution was extracted 3 times with chloroform, washed with water, 1N HCl, water, dried over Na$_2$SO$_4$. Recrystallization from CHCl$_3$-hexanes gave 5.3 g (83%) of the product.

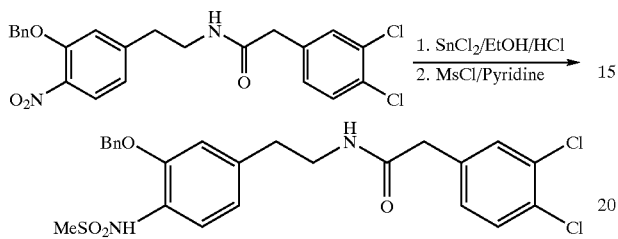

N-[2-(3-benzyloxy4-methanesulfonylamino-phenyl)-ethyl]-2-(3,4-dichloro-phenyl)-acetamide. A mixture of N-[2-(3-benzyloxy-4-nitro-phenyl)-ethyl]-2-(3,4-dichloro-phenyl)-acetamide (5.2 g, 0.0113 mol), SnCl$_2$2H$_2$O (25.6 g, 0.11 mol) in EtOH (250 mL) and 10% aqueous HCl (100 mL) was refluxed for 3 h and evaporated. The white residue was taken in to 1N NaOH. The reaction mixture was extracted with CHCl$_3$ (150 mL X 3). Combined extracts were washed with water, brine, dried over Na$_2$SO$_4$. The crude amine was crystallized from EtOAc-hexanes.

To the amine in dry pyridine (20 mL) at 0° C. methanesulfonyl chloride (0.73 ml, 0.00946 mol) was added dropwise. The reaction mixture was stirred overnight at room temperature. CHCl$_3$ was added. The reaction mixture was washed with 1N HCl, 1N NaOH, water, brine and dried over Na$_2$SO$_4$. Crystallization from CHCl$_3$-hexanes mixture gave 4 g (90%) of the product.

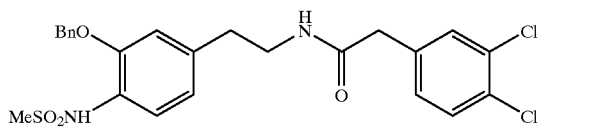

N-[6-benzyloxy-1-(3,4-dichloro-benzyl)-1,2,3,4-tetrahydro-isoquinolin-7-yl]-methanesulfonamide oxalate. A solution of N-[2-(3-benzyloxy-4-methanesulfonylamino-phenyl]-ethyl]-2-(3,4-dichloro-phenyl)-acetamide (3.84 g, 0.00756 mol) and 7 mL of POCl$_3$ in 50 mL of acetonitrile was refluxed for 5 h, cooled, concentrated, evaporated 3 times with MeOH, dissolved in 50 mL of MeOH, cooled with an ice bath. NaBH$_4$ (2.87 g, 0.0756 mol) was added by small portions. The reaction mixture was stirred for 2 h at room temperature and concentrated, CHCl$_3$ was added. The reaction mixture was washed with 10% solution of NaOH and 50% brine twice, water, dried over Na$_2$SO$_4$, filtered and concentrated. The residue was dissolved in CHCl$_3$ and a solution of (COOH)$_2$.2H$_2$O in MeOH was added. The product was crystallized chloroform-methanol—ethyl ether mixture. Yield 3.52 g (80%).

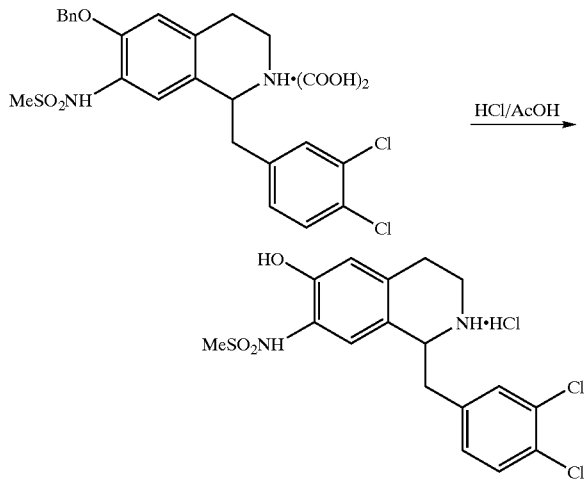

N-[1-(3,4-dichloro-benzyl)-6-hydroxy-1,2,3,4-tetrahydro-isoquinolin-7-yl]-methanesulfonamide hydrochloride. A solution of N-[6-benzyloxy-1-(3,4-dichloro-benzyl)-1,2,3,4-tetrahydro-isoquinolin-7-yl]-methanesulfonamide oxalate (0.5 g, 0.00085 mol) in 15 mL of acetic acid and 30 mL of conc. HCl was refluxed for 1 h, evaporated to dryness and the residue was crystallized from methanol-ether mixture. Yield 0.23 g (62%). mp 249–250° C. $^1$H NMR (Me$_2$SO-d$_6$) 300 MHz: δ 10.17 (s, 1H), 9.23 (brs, 2H), 8.84 (s, 1H), 7.75 (s, 1H), 7.61 (d, J=7.8 Hz, 1H), 7.42 (d, J=8.1 Hz, 1H), 7.10 (s, 1H), 6.75 (s, 1H), 4.70 (brs, 1H), 3.28–3.43 (brs, 4H), 3.10–3.22 (m, 1H), 2.96–3.04 (m, 1H), 2.90 (s, 3H). MS (ESI): 402 (MH$^+$).

Example 12

Preparation of N-[1-(3,5-Dibromo-4-methoxy-benzyl)-1,2,3,4-tetrahydro-isoquinolin-6-yl]-methanesulfonamide

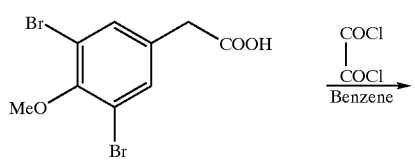

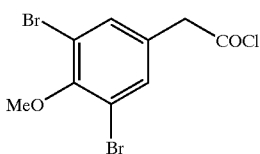

(3,5-Dibromo-4-methoxyphenyl)acetylchloride. 3,5-Dibromo-4-methoxyphenyl acetic acid (3.239 g, 0.01 mol) was refluxed with oxalyl chloride (2.03 g, 0.016 mol) in anhydrous benzene (50 mL) for 6 h. The reaction mixture was cooled, concentrated and evaporated 3 times with benzene to give an oil which was used for further reaction.

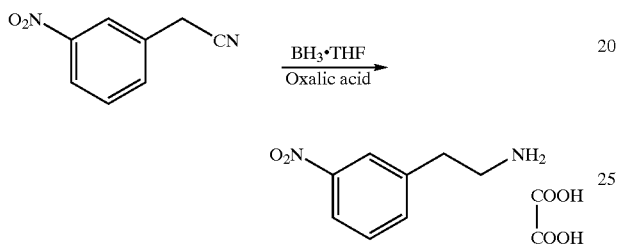

3-nitro-phenethylamine oxalate. 3-Nitrophenyl acetonitrile (6.486 g, 0.04 mol) was refluxed with borane-THF complex (40 mL, 0.04 mole) in anhydrous THF (80 mL) for 45 min under argon. The reaction mixture was quenched with methanol and concentrated. 3-Nitrophenylethyl amine was crystallized from the reaction mixture by adding oxalic acid (10 g, 0.08 mol). Yield 4.36 g, 85%.

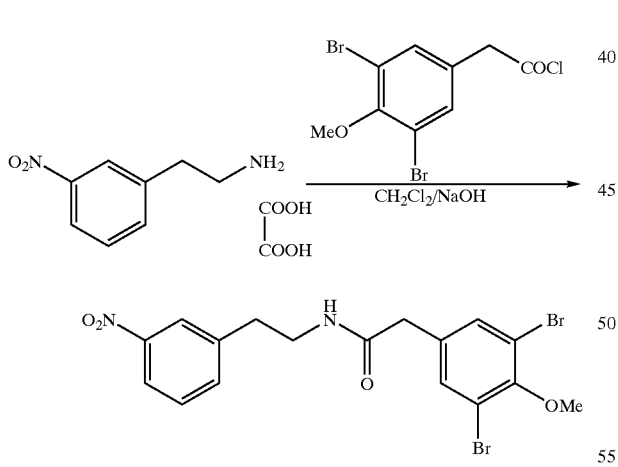

2-(3,5-dibromo-4-methoxy-phenyl)-N-[2-(3-nitrophenyl)-ethyl]-acetamide. To a suspension of 3-nitrophenethylamine oxalate (1.792 g, 0.007 mol) in methylene chloride (45 mL), 1 N NaOH (45 mL) was added. It was stirred at room temperature to get a clear solution. A solution of 3,5-dibromo-4-methoxyphenyl acetyl chloride (0.0072 mol) in methylene chloride was added. Stirring was continued overnight and the completion of the reaction was monitored by thin layer chromatography. The reaction mixture was washed with 1N HCl and 1N NaOH, extracted with methylene chloride. The combined extracts were dried over anhydrous sodium sulfate and concentrated. The solid obtained was crystallized from ethyl acetate-hexanes mixture. Yield 2.159 g, 65%.

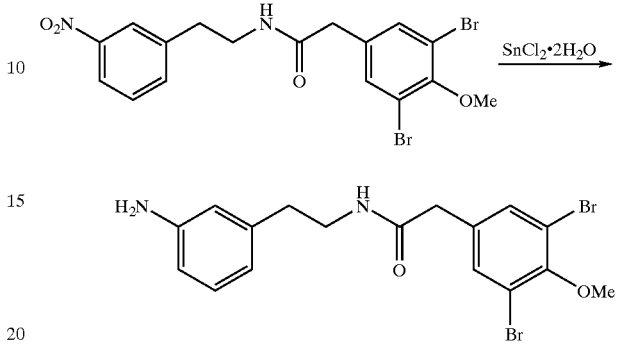

N-[2-(3-amino-phenyl)-ethyl]-2-(3,5-dibromo-4-methoxy-phenyl)-acetamide. 2-(3,5-dibromo-4-methoxy-phenyl)-N-[2-(3-nitrophenyl)-etbyl]-acetamide (1 g, 0.0021 mol) was refluxed with $SnCl_2 \cdot 2H_2O$ (1.4 g, 0.0063 mol) in a mixture of ethanol (15 mL) and HCl (0.3 mL) for 5 h. The solution was cooled and the pH was made slightly basic by the addition of 1N NaOH solution. The desired compound was extracted into methylene chloride, concentrated, dried over $Na_2SO_4$ and purified by column chromatography (silica gel, 1:1 ethyl acetate-hexanes mixture). Yield 0.580 g, 61.9%. MS m/e 464.9 [M+Na].

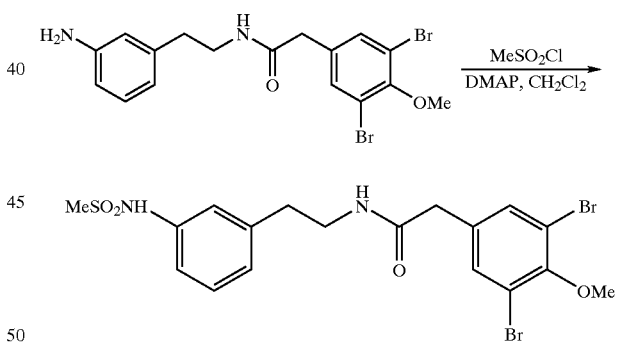

2-(3,5-dibromo-4-methoxy-phenyl)-N-[2-(3-methanesulfonylamino-phenyl)-ethyl]-acetamide. Methanesulfonyl chloride (0.0313 g, 0.000273 mol) was added to DMAP (0.0334 g, 0.000273 mol) in methylene chloride (6 mL). To the resulting white complex N-[2-(3-aminophenyl)-ethyl]-2-(3,5-dibromo-4-methoxy-phenyl)-acetamide (0.1 g, 0.000226 mol) in methylene chloride (6mL) was added dropwise. The reaction mixture was stirred for 18 h at room temperature, washed with 1 N HCl and 1 N NaOH. The organic layer was dried over anhydrous sodium sulfate, concentrated and purified by column chromatography (silica gel, 1:1 ethyl acetate-hexane mixture). Yield 0.058 g, 49%. MS m/e 518.7 [M+H].

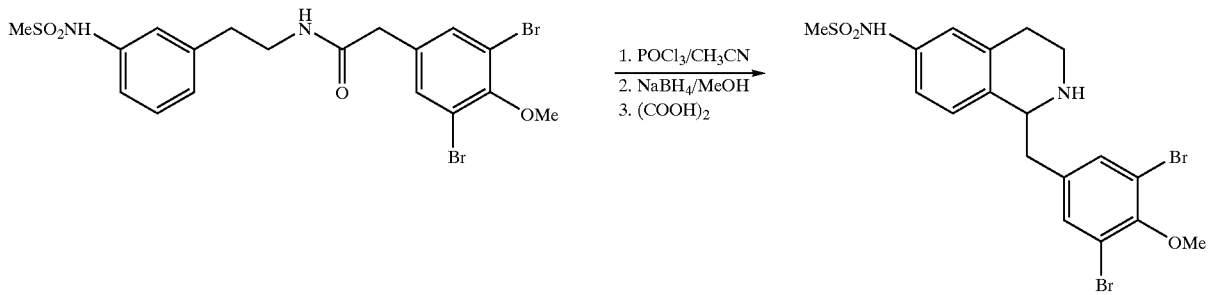

N-[1-(3,5-dibromo-4-methoxy-benzyl)-1,2,3,4-tetrahydro-isoquinolin-6-yl]-methanesulfonamide. To solution of 2-(3,5-dibromo-4-methoxy-phenyl)-N-[2-(3-methanesulfonylamino-phenyl)-ethyl]-acetamide in 15 mL of acetonitrile, phosphorus oxychloride is added. The reaction mixture is refluxed for 5 h. The residue after concentration is evaporated 3 times with MeOH, dissolved in 20 mL of MeOH, cooled with an ice bath, and $NaBH_4$ is added by small portions. The reaction mixture is stirred overnight at room temperature, concentrated, dissolved in chloroform, washed with 1N NaOH, dried over $Na_2SO_4$, filtered, and concentrated. The residue is dissolved in methanol, and a solution of $(COOH)_2 \cdot 2H_2O$ in methanol is added.

Example 13 $\beta_3$ Selectivity Testing Using cAMP Radioimmunoassay

Chinese Hamster Ovary (CHO) cells expressing either human $\beta_1$-, $\beta_2$-, or $\beta_3$-adrenoreceptor subtypes were used. Varying concentrations of each compound were added to the incubated cells and the cyclic AMP (cAMP) generated within the cells was extracted, and determined using a radioimmunoassay. Effective concentration-50 (EC-50) values were measured as the concentration (in nanomolar) of each drug that gave 50% of its maximum cAMP response. The maximal response (Max %) of each tested drug is expressed as a ratio of the drug response to that of a standard reference agonist (e.g., isoproterenol (Max %=100%)). If a compound has no activity for increasing cAMP at the highest concentration used, it is designated as "not active" or "na" in Table I below, which summarizes the testing results. See Konkar et al., Journal of Pharmacology and Experimental Therapeutics 291:875–883 (1999).

Generally speaking, compounds exhibiting a $\beta_3$ EC50 of about 20 or less, more preferably about 15 or less, and most preferably about 10 or less, are preferred. Compounds exhibiting no activity in relation to $\beta_1$ and $\beta_2$ receptors are also preferred.

TABLE I

| Compound | h-β3 cAMP EC50 (nM) | Max % | h-β2 cAMP EC50 (nM) | Max % | h-β1 cAMP EC50 (nM) | Max % |
|---|---|---|---|---|---|---|
| (structure) | 3 | 98 | na | 5 | na | 5 |
| (structure) | 4.65/0.43 | 116.5/93.5 | na | 18.9 | na | 3 |

TABLE I-continued

| Compound | h-β3 cAMP EC50 (nM) | Max % | h-β2 cAMP EC50 (nM) | Max % | h-β1 cAMP EC50 (nM) | Max % |
|---|---|---|---|---|---|---|
| (structure: 6-hydroxy-7-methanesulfonamido-1-(3,5-dibromo-4-methoxybenzyl)-1,2,3,4-tetrahydroisoquinoline) | 0.29 | 109.9 | na | 10.5, 23.9 | na | 11.54, 13.2 |
| (structure: 6-hydroxy-7-methanesulfonamido-1-(3,5-dibromo-4-methoxybenzyl)-1,2,3,4-tetrahydroisoquinoline variant) | 21.91 | 100.4 | na | 20.6 | na | 11.3 |
| (structure: N-methyl analog with 3,5-dibromo-4-methoxybenzyl) | na | 39.3 | na | 24.1 | na | 16.2 |
| (structure: 6-hydroxy-7-methanesulfonamido-1-(4-methoxybenzyl)-1,2,3,4-tetrahydroisoquinoline) | na | 23.96 | na | na | na | na |
| (structure: 6-hydroxy-7-methanesulfonamido-1-(3,4-dimethoxybenzyl)-1,2,3,4-tetrahydroisoquinoline) | 118.1 | 76.9 | na | 15.4 | na | 10.2 |

TABLE I-continued

| Compound | h-β3 cAMP EC50 (nM) | Max % | h-β2 cAMP EC50 (nM) | Max % | h-β1 cAMP EC50 (nM) | Max % |
|---|---|---|---|---|---|---|
| (structure: 6-hydroxy-7-methanesulfonamido-1-(3,4-dichlorobenzyl)-1,2,3,4-tetrahydroisoquinoline) | 9.91 | 91.96 | na | na | na | na |
| (structure: 6-amino-7-methanesulfonamido-1-(3,4-dichlorobenzyl)-1,2,3,4-tetrahydroisoquinoline) | na | 2.24 | na | 10.84 | na | 12.6 |
| (structure: 6-hydroxy-7-methanesulfonamido-1-(3,4-difluorobenzyl)-1,2,3,4-tetrahydroisoquinoline) | 24.45 | 78.3 | na | na | na | na |
| (structure: 6-hydroxy-7-methanesulfonamido-1-(3,5-difluorobenzyl)-1,2,3,4-tetrahydroisoquinoline) | 38.76 | 66.6 | na | na | na | na |
| (structure: 6-hydroxy-7-ethanesulfonamido-1-(3,5-dibromo-4-methoxybenzyl)-1,2,3,4-tetrahydroisoquinoline) | 1.51 | 101.69 | na | na | na | 8.4 |

TABLE I-continued

| Compound | h-β3 cAMP EC50 (nM) | Max % | h-β2 cAMP EC50 (nM) | Max % | h-β1 cAMP EC50 (nM) | Max % |
|---|---|---|---|---|---|---|
| [structure: phenylsulfonamide tetrahydroisoquinoline with 3,5-dibromo-4-methoxybenzyl] | 35.3 | 88.2 | na | 21.4 | na | 13.1 |
| [structure: 4-fluorophenylsulfonamide tetrahydroisoquinoline with 3,5-dibromo-4-methoxybenzyl] | 5.22 | 90.4 | na | 13.5 | na | 8.6 |
| [structure: bis(4-fluorophenylsulfonyl)amine tetrahydroisoquinoline with 3,5-dibromo-4-methoxybenzyl] | na | 8.7 | na | 5.8 | na | 12.1 |
| [structure: 4-methylphenylsulfonamide tetrahydroisoquinoline with 3,5-dibromo-4-methoxybenzyl] | 8.46 | 97.6 | na | 8 | na | 18.1 |
| [structure: 4-methoxyphenylsulfonamide tetrahydroisoquinoline with 3,5-dibromo-4-methoxybenzyl] | 8.09 | 88.27 | na | na | na | na |

TABLE I-continued
| Compound | h-β3 cAMP EC50 (nM) | Max % | h-β2 cAMP EC50 (nM) | Max % | h-β1 cAMP EC50 (nM) | Max % |
|---|---|---|---|---|---|---|
| 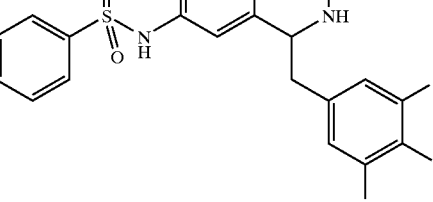 | 80.3 | 65.7 | na | na | na | na |
| 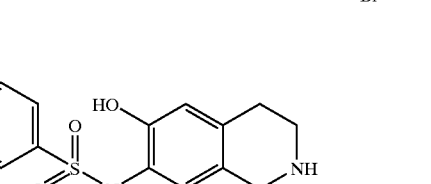 | 29.23 | 83.3 | na | 16.6 | na | 13 |
| 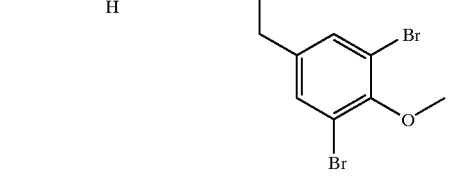 | 20.94 | 92.2 | na | na | na | na |
| 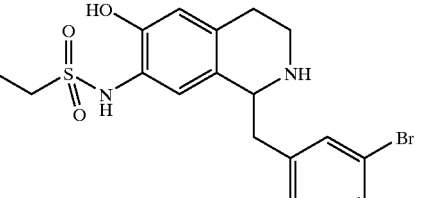 | 23.11 | 96.57 | na | na | na | na |
| 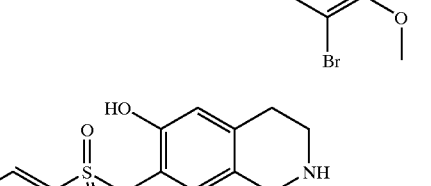 | 2.9 | 91 | na | 8 | na | 5 |

TABLE I-continued

| Compound | h-β3 cAMP EC50 (nM) | Max % | h-β2 cAMP EC50 (nM) | Max % | h-β1 cAMP EC50 (nM) | Max % |
|---|---|---|---|---|---|---|
| 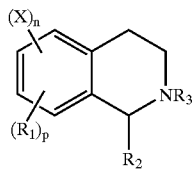 | na | 8.7 | na | 17.2 | na | 11 |

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A compound having the structure:

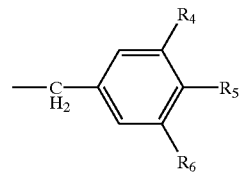

wherein:
  each $R_1$ is —NHS(O)$_m$R, wherein R is alkyl, substituted alkyl, alkoxy, substituted alkoxy, cycloalkyl, substituted cycloalkyl, aryl, substituted aryl, heteroaryl, substituted heteroaryl, heterocycle, or substituted heterocycle;
  each X is independently selected from the group consisting of halo, alkyl, substituted alkyl, alkoxy, substituted alkoxy, hydroxy, nitro, amino, and substituted amino;
  $R_2$ is benzyl or benzyl substituted with one or more substitutes selected from the group consisting of halo, $CF_3$, hydroxy, nitro, alkoxy, substituted alkoxy, alkyl, substituted alkyl, cycloalkyl, substituted cycloalkyl, aryl, substituted aryl, heteroaryl, substituted heteroaryl, heterocycle, substituted heterocycle, amino, and substituted amino of formula —NHR' or —NR'R', wherein each R' is alkyl, substituted alkyl, —C(O)Y, —C(O)NHY, or —C(O)SY, wherein Y is alkyl or substituted alkyl;
  $R_3$ is H or alkyl;
  n is 0–3;
  m is 1–2;
  p is 1–4;
  the sum of n and p is 1–4;
and pharmaceutically acceptable salts thereof.

2. A compound of claim 1, wherein m is 2.

3. A compound of claim 1, wherein n is 1 and X is hydroxy.

4. A compound of claim 1, wherein R is C1–C6alkyl, substituted C1–C6alkyl, phenyl, substituted phenyl, benzyl, or substituted benzyl.

5. A compound of claim 1, wherein R is selected from the group consisting of methyl, ethyl, propyl, butyl, phenyl, and benzyl, wherein the phenyl or benzyl group can be substituted with one or more C1–C6alkyl, C1–C6 alkoxy, hydroxy, halo, nitro, $CF_3$, —O—$CF_3$, amino, or amino substituted with one or two C1–C6alkyl.

6. A compound of claim 1, wherein the aromatic ring of $R_2$ is substituted with one or more alkoxy or halo groups.

7. A compound of claim 1, wherein $R_2$ has the structure:

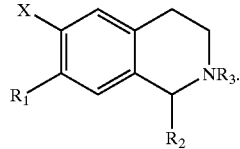

wherein $R_1$, $R_5$, and $R_6$ are independently selected alkoxy or halo.

8. A compound of claim 7, wherein $R_1$ and $R_6$ are halo and $R_5$ is C1–C6alkoxy.

9. A compound of claim 8, wherein $R_1$ and $R_6$ are bromo.

10. A compound of claim 8, wherein $R_5$ is methoxy.

11. A compound of claim 1, having the structure:

12. A compound of claim 11, wherein m is 2.

13. A compound of claim 11, wherein X is hydroxy.

14. A compound of claim 11, wherein R is C1–C6alkyl, substituted C1–C6alkyl, phenyl, substituted phenyl, benzyl, or substituted benzyl.

15. A compound of claim 11, wherein R is selected from the group consisting of methyl, ethyl, propyl, butyl, phenyl, and benzyl, wherein the phenyl or benzyl group can be substituted with one or more C1–C6alkyl, C1–C6 alkoxy, hydroxy, halo, nitro, $CF_3$, —O—$CF_3$, amino, or amino substituted with one or two C1–C6alkyl.

16. A compound of claim 11, wherein the aromatic ring of $R_2$ is substituted with one or more alkoxy or halo groups.

17. A compound of claim 11, wherein $R_2$ has the structure:

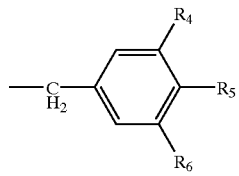

wherein $R_4$, $R_5$, and $R_6$ are independently selected alkoxy or halo.

18. A compound of claim 17, wherein $R_4$ and $R_6$ are halo and $R_5$ is C1–C6alkoxy.

19. A compound of claim 18, wherein $R_4$ and $R_6$ are bromo.

20. A compound of claim 18, wherein $R_5$ is methoxy.

21. A compound of claim 1, having the structure:

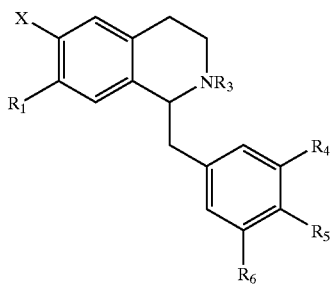

wherein:
X is hydroxy;
$R_1$ is —NHS(O)$_2$R, wherein R is selected from the group consisting of C1–C6alkyl, C1–C6alkoxy, phenyl, phenyl substituted with one or more C1–C6alkyl, C1–C6alkoxy, halo, $CF_3$, or —O—$CF_3$, benzyl, and benzyl substituted with one or more C1–C6alkyl, C1–C6alkoxy, halo, $CF_3$, or —O—$CF_3$;
$R_3$ is H or methyl; and
$R_4$, $R_5$ and $R_6$ are independently selected alkoxy or halo.

22. A pharmaceutical composition, comprising a pharmaceutically acceptable carrier and at least one compound having the structure:

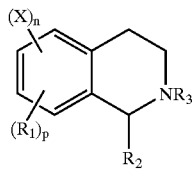

wherein:
each $R_1$ is —NHS(O)$_m$R, wherein R is alkyl, substituted alkyl, alkoxy, substituted alkoxy, cycloalkyl, substituted cycloalkyl, aryl, substituted aryl, heteroaryl, substituted heteroaryl, heterocycle, or substituted heterocycle;

each X is independently selected from the group consisting of halo, alkyl, substituted alkyl, alkoxy, substituted alkoxy, hydroxy, nitro, amino, and substituted amino;

$R_2$ is benzyl or benzyl substituted with one or more substituents selected from the group consisting of halo, $CF_3$, hydroxy, nitro, alkoxy, substituted alkoxy, alkyl, substituted alkyl, cycloalkyl, substituted cycloalkyl, aryl, substituted aryl, heteroaryl, substituted heteroaryl, heterocycle, substituted heterocycle, amino, and substituted amino of formula —NHR' or —NR'R', wherein each R' is alkyl, substituted alkyl, —C(O)Y, —C(O)NHY, or —C(O)SY, wherein Y is alkyl or substituted alkyl;

$R_3$ is H or alkyl;

n is 0–3;

m is 1–2;

p is 1–4;

the sum of n and p is 1–4;

and pharmaceutically acceptable salts thereof.

23. A pharmaceutical composition or claim 22, wherein m 2.

24. A pharmaceutical composition of claim 22, wherein n is 1 and X is hydroxy.

25. A pharmaceutical composition of claim 22, wherein R is C1–C6alkyl, substituted C1–C6alkyl, phenyl, substituted phenyl, benzyl, or substituted benzyl.

26. A pharmaceutical composition of claim 22, wherein R is selected from the group consisting of methyl, ethyl, propyl, butyl, phenyl, and benzyl, wherein the phenyl or benzyl group can be substituted with one or more C1–C6alkyl, C1–C6alkoxy, hydroxy, halo, nitro, $CF_3$, —O—$CF_3$, amino, or amino substituted with one or two C1–C6alkyl.

27. A pharmaceutical composition of claim 22, wherein the aromatic ring of $R_2$ is substituted with one or more alkoxy or halo groups.

28. A pharmaceutical composition or claim 22, wherein $R_2$ has the structure:

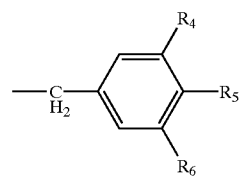

wherein $R_4$, $R_5$, and $R_6$, are independently selected alkoxy or halo.

29. A pharmaceutical composition of claim 28, wherein $R_4$ and $R_6$ are halo and $R_5$ is C1–C6alkoxy.

30. A pharmaceutical composition of claim 28, wherein $R_4$ and $R_6$ are bromo.

31. A pharmaceutical composition or claim 28, wherein $R_5$ is methoxy.

32. A pharmaceutical composition of claim 22, wherein said compound has the structure:

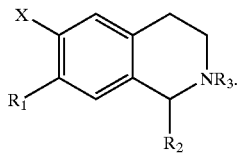

33. A pharmaceutical composition of claim 32, wherein m is 2.

34. A pharmaceutical composition of claim 32, wherein X is hydroxy.

35. A pharmaceutical composition of claim 32, wherein R is C1–C6alkyl, substituted C1–C6alkyl, phenyl, substituted phenyl, benzyl, or substituted benzyl.

36. A pharmaceutical composition of claim 32, wherein R is selected from the group consisting of methyl, ethyl, propyl, butyl, phenyl, and benzyl, wherein the phenyl or benzyl group can be substituted with one or more C1–C6alkyl, C1–C6 alkoxy, hydroxy, halo, nitro, $CF_3$, —O—$CF_3$, amino, or amino substituted with one or two C1–C6alkyl.

37. A pharmaceutical composition of claim 32, wherein the aromatic ring of $R_2$ is substituted with one or more alkoxy or halo groups.

38. A pharmaceutical composition of claim 32, wherein $R_2$ has the structure:

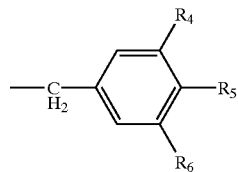

wherein $R_4$, $R_5$, and $R_6$ are independently selected alkoxy or halo.

39. A pharmaceutical composition of claim 38, wherein $R_4$ and $R_6$ are halo and $R_5$ is C1–C6alkoxy.

40. A pharmaceutical composition of claim 39, wherein $R_4$ and $R_6$ are bromo.

41. A pharmaceutical composition of claim 39, wherein $R_5$ is methoxy.

42. A pharmaceutical composition of claim 22, wherein said compound has the structure:

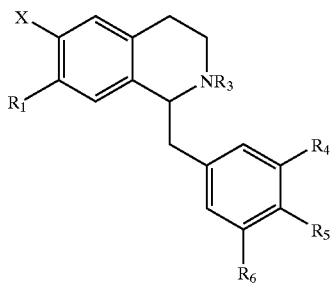

wherein:
   X is hydroxy;
   $R_1$ is —NHS(O)$_2$R, wherein R is selected from, the group consisting of C1–C6alkyl, C1–C6alkoxy, phenyl, phenyl substituted with one or more C1–C6alkyl, C1–C6alkoxy halo, $CF_3$, or —O—$CF_3$, benzyl, and benzyl substituted with one or more C1–C6alkyl, C1–C6alkoxy, halo, $CF_3$, Or —O—$CF_3$;
   $R_3$ is H or methyl; and
   $R_4$, $R_5$, and $R_6$ are independently selected alkoxy or halo.

43. A method for stimulating, regulating and modulating metabolism of fats in adipose tissue in mammals, comprising administering to a mammal an effective amount of a $β_3$-adrenoreceptor agonist having the structure:

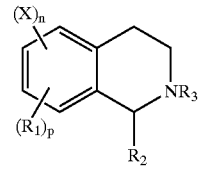

wherein:
   each $R_1$ is —NHS(O)$_m$R, wherein R is alkyl, substituted alkyl, alkoxy, substituted alkoxy, cycloalkyl, substituted cycloalkyl, aryl, substituted aryl, heteroaryl, substituted heteroaryl, heterocycle, or substituted heterocycle;
   each X is independently selected from the group consisting of halo, alkyl, substituted alkyl, alkoxy, substituted alkoxy, hydroxy, nitro, amino, and substituted amino;
   $R_2$ is benzyl or benzyl substituted with one or more substituents selected from the group consisting of halo, $CF_3$, hydroxy, nitro, alkoxy, substituted alkoxy, alkyl, substituted alkyl, cycloalkyl, substituted cycloalkyl, aryl, substituted aryl, heteroaryl, substituted heteroaryl, heterocycle, substituted heterocycle, amino, and substituted amino of formula —NHR' or —NR'R', wherein each R' is alkyl, substituted alkyl, —C(O)Y, —C(O)NHY, or —C(O)SY, wherein Y is alkyl or substituted alkyl;
   $R_3$ is H or alkyl;
   n is 0–3;
   m is 1–2;
   p is 1–4;
   the sum of n and p is 1–4;
   and pharmaceutically acceptable salts thereof.

44. A method of claim 43, wherein m is 2.

45. A method of claim 43, wherein n is 1 and X is hydroxy.

46. A method of claim 43, wherein R is C1–C6alkyl, substituted C1–C6alkyl, phenyl, substituted phenyl, benzyl, or substituted benzyl.

47. A method of claim 43, wherein R is selected from the group consisting of methyl, ethyl, propyl, butyl, phenyl, and benzyl, wherein the phenyl or benzyl group can be substituted with one or more C1–C6alkyl, C1–C6 alkoxy, hydroxy, halo, nitro, $CF_3$, —O—$CF_3$, amino, or amino substituted with one or two C1–C6alkyl.

48. A method of claim 43, wherein the aromatic ring of $R_2$ is substituted with one or more alkoxy or halo groups.

49. A method of claim 43, wherein $R_2$ has the structure:

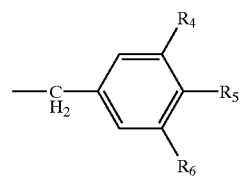

wherein $R_4$, $R_5$, and $R_6$ are independently selected alkoxy or halo.

50. A method of claim 49, wherein $R_4$ and $R_6$ are halo and $R_5$ is C1–C6alkoxy.

51. A method of claim 50, wherein $R_4$ and $R_6$ are bromo.
52. A method of claim 50, wherein $R_5$ is methoxy.
53. A method of claim 43, wherein the agonist has the structure:

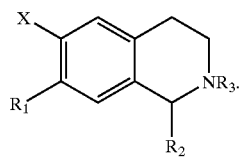

54. A method of claim 53, wherein m is 2.
55. A method of claim 53, wherein X is hydroxy.
56. A method of claim 53, wherein R is C1–C6alkyl, substituted C1–C6alkyl, phenyl, substituted phenyl, benzyl, or substituted benzyl.
57. A method of claim 53, wherein R is selected from the group consisting of methyl, ethyl, propyl, butyl, phenyl, and benzyl, wherein the phenyl or benzyl group can be substituted with one or more C1–C6alkyl, C1–C6 alkoxy, hydroxy, halo, nitro, $CF_3$, —O—$CF_3$, amino, or amino substituted with one or two C1–C6alkyl.
58. A method of claim 53, wherein the aromatic ring of $R_2$ is substituted with one or more alkoxy or halo groups.
59. A method of claim 53, wherein $R_2$ has the structure:

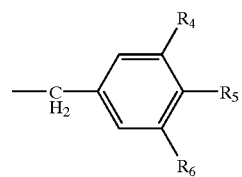

wherein $R_4$, $R_5$, and $R_6$ are independently selected alkoxy or halo.
60. A method of claim 59, wherein $R_4$ and $R_6$ are halo and $R_5$ is C1–C6alkoxy.
61. A method of claim 59, wherein $R_4$ and $R_6$ are bromo.
62. A method of claim 59, wherein $R_5$ is methoxy.
63. A method of claim 43, wherein the agonist has the structure:

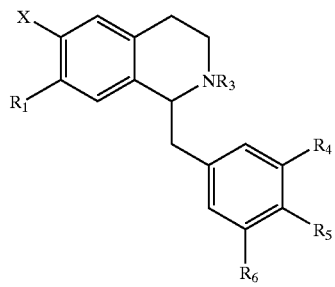

wherein;
X is hydroxy;
$R_1$ is —$NHS(O)_2R$, wherein R is selected from the group consisting of C1–C6alkyl, C1–C6alkoxy, phenyl, phenyl substituted with one or more C1–C6alkyl, C1–C6alkoxy, halo, $CF_3$, or —O—$CF_3$, benzyl, and benzyl substituted with one or more C1–C6alkyl, C1–C6alkoxy, halo, $CF_3$, or —O—$CF_3$;
$R_3$ is H or methyl; and
$R_4$, $R_5$, and $R_6$ are independently selected alkoxy or halo.

64. A compound of claim 1, selected from the group consisting of:

N-[1-(3,5-dibromo-4-methoxy-benzyl)-6-hydroxy-1,2,3,4-tetrahydro-isoquinolin-7-yl]-methanesulfonamide;

N-[1-(3,5-dibromo-4-methoxy-benzyl)-6-hydroxy-1,2,3,4-tetrahydro-isoquinolin-7-yl]-benzenesulfonamide;

N-[1-(3,5-dibromo-4-methoxy-benzyl)-6-hydroxy-1,2,3,4-tetrahydro-isoquinolin-7-yl]-4-methyl-benzenesulfonamide;

N-[1-(3,5-dibromo-4-methoxy-benzyl)-6-hydroxyl-1,2,3,4-tetrahydro-isoquinolin-7-yl]-4-methoxy-benzenesulfonamide;

N-[1-(3,5-dibromo-4-methoxy-benzyl)-6-hydroxy-1,2,3,4-tetrahydro-isoquinolin-7-yl]-4-methoxy-benzenesulfonamide;

N-[1-(3,5-dibromo-4-methoxy-benzyl-6-hydroxy-1,2,3,4-tetrahydro-isoquinolin-7-yl]-4-trifluoromethoxy-benzenesulfonamide;

N-[1-(3,5-dibromo-4-methoxy-benzyl)-6-hydroxy-1,2,3,4-tetrahydroisoquinolin-7-yl]-4-fluoro-benzenesulfonamide;

Ethanesulfonic acid [1-(3,5-dibromo-4-methoxy-benzyl)-6-hydroxy-1,2,3,4-tetrahydro-isoquinolin-7-yl]-amide;

N-[1-(3,5-dibromo-4-methoxy-benzyl)-6-hydroxy-1,2,3,4-tetrahydro-isoquinolin-7-yl]-C-phenyl-methanesulfonamide;

2-phenyl-ethenesulfonic acid [1-(3,5-dibromo-4-methoxy-benzyl)-6-hydroxy-1,2,3,4-tetrahydro-isoquinolin-7-yl]-amide;

N-[1-(3,4-dichloro-benzyl)-6-hydroxy-1,2,3,4-tetrahydro-isoquinolin-7-yl]-methanesulfonamide;

N-[1-(3,5-dibromo-4-methoxy-benzyl)-1,2,3,4-tetrahydro-isoquinolin-6-yl]-methanesulfonamide; and pharmaceutically acceptable salts thereof.

65. A pharmaceutical composition of claim 22, wherein said compound is selected from the group consisting of:

N-[1-(3,5-dibromo-4-methoxy-benzyl)-6-hydroxy-1,2,3,4-tetrahydro-isoquinolin-7-yl]-methanesulfonamide;

N-[1-(3,5-dibromo-4-methoxy-benzyl)-6-hydroxy-1,2,3,4-tetrahydro-isoquinolin-7-yl]-benzenesulfonamide;

N-[1-(3,5-dibromo-4-methoxy-benzyl)-6-hydroxy-1,2,3,4-tetrahydro-isoquinolin-7-yl]-4-methyl-benzenesulfonamide;

N-[1-(3,5-dibromo-4-methoxy-benzyl)-6-hydroxyl-1,2,3,4-tetrahydro-isoquinolin-7-yl]-4-methoxy-benzenesulfonamide;

N-[1-(3,5-dibromo-4-methoxy-benzyl)-6-hydroxy-1,2,3,4-tetrahydro-isoquinolin-7-yl]-4-methoxy-benzenesulfonamide;

N-[1-(3,5-dibromo-4-methoxy-benzyl-6-hydroxy-1,2,3,4-tetrahydro-isoquinolin-7-yl]-4-trifluoromethoxy-benzenesulfonamide;

N-[1-(3,5-dibromo-4-methoxy-benzyl)-6-hydroxy-1,2,3,4-tetrahydroisoquinolin-7-yl]-4-fluoro-benzenesulfonamide;

Ethanesulfonic acid [1-(3,5-dibromo-4-methoxy-benzyl)-6-hydroxy-1,2,3,4-tetrahydro-isoquinolin-7-yl]-amide;

N-[1-(3,5-dibromo-4-methoxy-benzyl)-6-hydroxy-1,2,3,4-tetrahydro-isoquinolin-7-yl]-C-phenyl-methanesulfonamide;

2-phenyl-ethenesulfonic acid [1-(3,5-dibromo-4-methoxy-benzyl)-6-hydroxy-1,2,3,4-tetrahydro-isoquinolin-7-yl]-amide;

N-[1-(3,4-dichloro-benzyl)-6-hydroxy-1,2,3,4-tetrahydro-isoquinolin-7-yl]-methanesulfonamide;

N-[1-(3,5-dibromo-4-methoxy-benzyl)-1,2,3,4-tetrahydro-isoquinolin-6-yl]-methanesulfonamide; and pharmaceutically acceptable salts thereof.

66. A method of claim 43, wherein the agonist is selected from the group consisting of:

N-[1-(3,5-dibromo-4-methoxy-benzyl)-6-hydroxy-1,2,3,4-tetrahydro-isoquinolin-7-yl]-methanesulfonamide;

N-[1-(3,5-dibromo-4-methoxy-benzyl)-6-hydroxy-1,2,3,4-tetrahydro-isoquinolin-7-yl]-benzenesulfonamide;

N-[1-(3,5-dibromo-4-methoxy-benzyl)-6-hydroxy-1,2,3,4-tetrahydro-isoquinolin-7-yl]-4-methyl-benzenesulfonamide;

N-[1-(3,5-dibromo-4-methoxy-benzyl)-6-hydroxyl-1,2,3,4-tetrahydro-isoquinolin-7-yl]-4-methoxy-benzenesulfonamide;

N-[1-(3,5-dibromo-4-methoxy-benzyl)-6-hydroxy-1,2,3,4-tetrahydro-isoquinolin-7-yl]-4-methoxy-benzenesulfonamide;

N-[1-(3,5-dibromo-4-methoxy-benzyl-6-hydroxy-1,2,3,4-tetrahydro-isoquinolin-7-yl]-4-trifluoromethoxy-benzenesulfonamide;

N-[1-(3,5-dibromo-4-methoxy-benzyl)-6-hydroxy-1,2,3,4-tetrahydroisoquinolin-7-yl]-4-fluoro-benzenesulfonamide;

Ethanesulfonic acid [1-(3,5-dibromo-4-methoxy-benzyl)-6-hydroxy-1,2,3,4-tetrahydro-isoquinolin-7-yl]-amide;

N-[1-(3,5-dibromo-4-methoxy-benzyl)-6-hydroxy-1,2,3,4-tetrahydro-isoquinolin-7-yl]-C-phenyl-methanesulfonamide;

2-phenyl-ethenesulfonic acid [1-(3,5-dibromo-4-methoxy-benzyl)-6-hydroxy-1,2,3,4-tetrahydro-isoquinolin-7-yl]-amide;

N-[1-(3,4-dichloro-benzyl)-6-hydroxy-1,2,3,4-tetrahydro-isoquinolin-7-yl]-methanesulfonamide;

N-[1-(3,5-dibromo-4-methoxy-benzyl)-1,2,3,4-tetrahydro-isoquinolin-6-yl]-methanesulfonamide; and pharmaceutically acceptable salts thereof.

* * * * *

UNITED STATES PATENT AND TRADEMARK OFFICE
CERTIFICATE OF CORRECTION

PATENT NO.      : 6,596,734 B1
DATED           : July 22, 2003
INVENTOR(S)     : Feller et al.

It is certified that error appears in the above-identified patent and that said Letters Patent is hereby corrected as shown below:

Title page,
Item [56], References Cited, OTHER PUBLICATIONS,
"He, et al.," reference, "4-tetrahydroisoquiniolin" should read
-- 4-tetrahydroisoquinolin --;
"Kajigaeshi et al.," reference, "Benzyltrimethylammonaium" should read
-- Benzyltrimethylammonium --.

Column 9,
Line 16, "II." should read -- III. --.

Column 26,
Line 42, "tetrahydro-isoguinolin" should read -- tetrahydro-isoquinolin --.

Column 28,
Line 43, "tetrahydroisoiuinolin" should read -- tetrahydroisoquinolin --.

Column 36,
Line 32, "tetrahydro-isoguinolin" should read -- tetrahydro-isoquinolin --.

Column 38,
Line 58, "tetrahydro-isoguinolin" should read -- tetrahydro-isoquinolin --.

Column 51,
Line 54, "substitutes" should read -- substituents --.

Column 52,
Lines 48, 50 and 52, "$R_1$" should read -- $R_4$ --.

Column 54,
Lines 24, 44 and 63, "or" should read -- of --.

Column 55,
Line 62, after "from" cancel the comma ",";
Line 65, after "C1-C6alkoxy" insert a comma -- , --;
Line 67, "Or" should read -- or --.

UNITED STATES PATENT AND TRADEMARK OFFICE
CERTIFICATE OF CORRECTION

PATENT NO.    : 6,596,734 B1
DATED         : July 22, 2003
INVENTOR(S)   : Feller et al.

It is certified that error appears in the above-identified patent and that said Letters Patent is hereby corrected as shown below:

Column 57,
Line 58, after "wherein" the semicolon ";" should be a colon -- : --.

Column 58,
Line 15, "methoxy-" should read -- trifluoromethoxy- --;
Line 51, "methoxy-" should read -- trifluoromethoxy --;
Line 17, after "benzyl" insert a close parenthesis;
Lines 18 and 54, "trifluoromethoxy-" should read -- trifluoromethyl- --.

Column 59,
Line 20, "methoxy-" should read -- trifluoromethoxy- --.

Column 60,
Line 2, "trifluoromethoxy-" should read -- trifluoromethyl- --.

Signed and Sealed this

Twenty-eighth Day of October, 2003

JAMES E. ROGAN
*Director of the United States Patent and Trademark Office*